US012648823B2

(12) United States Patent
Yajima et al.

(10) Patent No.: US 12,648,823 B2
(45) Date of Patent: Jun. 9, 2026

(54) CONTROL SYSTEM, CONTROL DEVICE, AND ACTUATOR

(71) Applicant: Sony Group Corporation, Tokyo (JP)

(72) Inventors: Shunsuke Yajima, Tokyo (JP); Jun Arai, Tokyo (JP)

(73) Assignee: Sony Group Corporation, Tokyo (JP)

( * ) Notice: Subject to any disclaimer, the term of this patent is extended or adjusted under 35 U.S.C. 154(b) by 90 days.

(21) Appl. No.: 18/708,608

(22) PCT Filed: Nov. 8, 2022

(86) PCT No.: PCT/JP2022/041566
§ 371 (c)(1),
(2) Date: May 9, 2024

(87) PCT Pub. No.: WO2023/090204
PCT Pub. Date: May 25, 2023

(65) Prior Publication Data
US 2025/0009446 A1      Jan. 9, 2025

(30) Foreign Application Priority Data

Nov. 16, 2021      (JP) ................................. 2021-186535

(51) Int. Cl.
*B25J 9/10*          (2006.01)
*A61B 34/30*        (2016.01)
(Continued)

(52) U.S. Cl.
CPC .............. *A61B 34/30* (2016.02); *B25J 9/102* (2013.01); *B25J 9/126* (2013.01); *A61B 2034/301* (2016.02); *A61B 2034/305* (2016.02)

(58) Field of Classification Search
CPC ... B25J 9/102; B25J 9/126; B25J 9/103; B25J 3/04; B25J 9/1633; B25J 17/00;
(Continued)

(56) References Cited

U.S. PATENT DOCUMENTS

| | | | | |
|---|---|---|---|---|
| 2013/0074636 A1* | 3/2013 | Doi | ........................ | B25J 9/1025 74/490.03 |
| 2018/0023753 A1* | 1/2018 | Kawamori | ........... | B25J 17/0258 248/280.11 |

(Continued)

FOREIGN PATENT DOCUMENTS

| | | |
|---|---|---|
| CN | 109483597 A | 3/2019 |
| JP | H03-065041 A | 3/1991 |

(Continued)

OTHER PUBLICATIONS

International Search Report and Written Opinion mailed on Jan. 31, 2023, received for International Application No. PCT/JP2022/041566, filed on Nov. 8, 2022, 11 pages including English Translation.

*Primary Examiner* — Khoi H Tran
*Assistant Examiner* — Tanner L Cullen
(74) *Attorney, Agent, or Firm* — XSENSUS LLP

(57) ABSTRACT

A control system of an aspect according to the present disclosure includes a robot including an actuator, and an estimation section that estimates external force received by the robot on the basis of state information of the robot, in which the actuator includes an encoder on an output shaft side, a speed reducer that has backdrivability, that is coupled to the encoder on the output shaft side, and that is a load element, a motor coupled to the speed reducer, and an encoder on an input shaft side which encoder is coupled to the motor.

16 Claims, 16 Drawing Sheets

52

$J_m,q_m$ 53   $R_g$        $K_s$         $J_l,q_l$ $\tau_m^{ref}$ ⟹ | Motor | Gear | ∿∿∿ | Load |

$d_m$                        $d_l + \tau^{ext}$

J : Inertia          $\tau_m^{ref}$ : Input          $O_m$ : Motor q : Position         d : Disturbance              $O_l$ : Load $K_s, R_g$ : Gear param.

(51) Int. Cl.
*B25J 9/12* (2006.01)
*B25J 17/00* (2006.01)

(58) Field of Classification Search
CPC . G05B 19/404; A61B 34/77; A61B 2090/066;
A61B 34/03; A61B 34/07; H02P 21/20
See application file for complete search history.

(56) References Cited

U.S. PATENT DOCUMENTS

| | | | | |
|---|---|---|---|---|
| 2018/0241283 A1* | 8/2018 | Kokubo | ................ | G01D 5/145 |
| 2018/0325713 A1* | 11/2018 | Gregg | .................. | A61F 5/0102 |
| 2018/0361576 A1* | 12/2018 | Sakai | .................... | B25J 9/1694 |
| 2019/0064756 A1* | 2/2019 | Tajima | ................ | G05B 13/041 |
| 2019/0368594 A1* | 12/2019 | Sakata | .................... | B25J 9/042 |
| 2019/0391566 A1* | 12/2019 | Ishikawa | ............ | G05B 19/4155 |
| 2020/0272122 A1* | 8/2020 | Oikawa | ............. | G05B 19/4065 |
| 2021/0276183 A1* | 9/2021 | Takahashi | ............. | B25J 9/1653 |
| 2022/0226993 A1* | 7/2022 | Madsen | ................ | B25J 9/1641 |

FOREIGN PATENT DOCUMENTS

| | | | | |
|---|---|---|---|---|
| JP | H0365041 A | * | 3/1991 | ............ G02B 26/10 |
| JP | H07-319558 A | | 12/1995 | |
| JP | 2019-049852 A | | 3/2019 | |
| JP | 2021-049597 A | | 4/2021 | |
| WO | 2012/127532 A1 | | 9/2012 | |
| WO | 2015/133291 A1 | | 9/2015 | |
| WO | WO-2020213062 A1 | * | 10/2020 | .......... H02P 23/0018 |

* cited by examiner

TORQUE SENSORLESS                    TORQUE SENSOR IS MOUNTED

5 TO 10mm

MOTOR POSITION $q_m$
MOTOR SPEED $\dot{q}_m$
LOAD POSITION $q_l$
LOAD SPEED $\dot{q}_l$
MOTOR ACCELERATION $\ddot{q}_m^{ref}$

LSTM

N1

$\widehat{d'_m} = R_g^{-1} J_l \ddot{q}_l + d_m + R_g^{-1} d_l$

DISTURBANCE

LEARN DISTURBANCE
(LOAD INERTIA/FRICTION/MODELING ERROR)

ARM CONTROL DEVICE

5037

5039

5041

5043

CCU

LIGHT SOURCE DEVICE

5053

RECORDING DEVICE

5055

OUTPUT DEVICE

1

CONTROL SYSTEM, CONTROL DEVICE, AND ACTUATOR

CROSS-REFERENCE TO RELATED APPLICATIONS

The present application is a national stage application, pursuant to 35 U.S.C. § 371, of International Patent Application No. PCT/JP2022/041566, filed Nov. 8, 2022, which claims priority from Japanese Patent Application No. 2021-186535, filed Nov. 16, 2021, the entire contents of each are incorporated herein by reference.

FIELD

The present disclosure relates to a control system, a control device, and an actuator.

BACKGROUND

For example, in a robot such as a medical robot, an external force detector that secures high backdrivability of an actuator is required at the same time as downsizing of the robot in order to improve safety and operability. In a case where a torque sensor is used as the external force detector, the torque sensor is usually mounted on each actuator of a robot joint. In addition, in a case where a force sensor is used as the external force detector, the force sensor is mounted at a distal end of the robot. Note that a model-based method of estimating external force without a force sensor has also been proposed (see, for example, Patent Literature 1).

CITATION LIST

Patent Literature

Patent Literature 1: Japanese Patent Application Laid-open No. 2019-49852

SUMMARY

Technical Problem

However, since a torque sensor is mounted on each actuator of a robot joint as described above, a cost is increased according to the number of joints. In addition, when a force sensor is mounted at a distal end of the robot, external force cannot be detected at other portions. In both cases, an introduction and maintenance cost is high, and installation is mechanically restricted. In addition, in the model-based method of estimating the external force without the force sensor, it is difficult to perform modeling of mechanical friction, and it is difficult to appropriately estimate the external force received by the robot with sufficient accuracy for a medical use due to an influence of friction and a modeling error.

Thus, the present disclosure proposes a control system, a control device, and an actuator capable of appropriately estimating external force received by a robot without using a torque sensor or a force sensor.

Solution to Problem

A control system according to the embodiment of the present disclosure includes: a robot having an actuator; and an estimation section that estimates external force received by the robot on a basis of state information of the robot, wherein the actuator includes an encoder on an output shaft side, a speed reducer coupled to the encoder on the output shaft side and having backdrivability, a motor coupled to the speed reducer, and an encoder on an input shaft side which encoder is coupled to the motor.

A control device according to the embodiment of the present disclosure includes: an estimation section that estimates, on a basis of state information of a robot having an actuator, external force received by the robot, wherein the actuator includes an encoder on an output shaft side, a speed reducer coupled to the encoder on the output shaft side and having backdrivability, a motor coupled to the speed reducer, and an encoder on an input shaft side which encoder is coupled to the motor.

An actuator according to the embodiment of the present disclosure includes: an encoder on an output shaft side; a speed reducer coupled to the encoder on the output shaft side and having backdrivability; a motor coupled to the speed reducer; and an encoder on an input shaft side which encoder is coupled to the motor.

BRIEF DESCRIPTION OF DRAWINGS

FIG. 12 is a diagram illustrating an example of an external torque estimator according to the one embodiment.

FIG. 13 is a diagram illustrating an example of a torque control system according to the one embodiment.

FIG. 16 is a diagram illustrating an example of a schematic configuration of an endoscope system.

DESCRIPTION OF EMBODIMENTS

In the following, embodiments of the present disclosure will be described in detail on the basis of the drawings. Note that the control system, the control device, the actuator, and the like according to the present disclosure are not limited by these embodiments. Also, in each of the following embodiments, overlapped description is omitted by assignment of the same reference sign to parts that are basically the same.

Each of one or a plurality of embodiments (including examples and modification examples) described in the following can be performed independently. On the other hand, at least a part of the plurality of embodiments described in the following may be appropriately combined with at least a part of the other embodiments. The plurality of embodiments may include novel features different from each other. Thus, the plurality of embodiments can contribute to solving different objects or problems, and can exhibit different effects.

The present disclosure will be described in the following order of items.

1. Embodiment
1-1. Configuration example of a control system
1-2. Configuration example of a robot
1-3. Configuration example of an actuator
1-4. Processing example of the control system
1-5. Action and effect
2. Other Embodiments
3. Application example
4. Configuration example of hardware
5. Appendix

1. Embodiment

<1-1. Configuration Example of a Control System>

Figure 1:
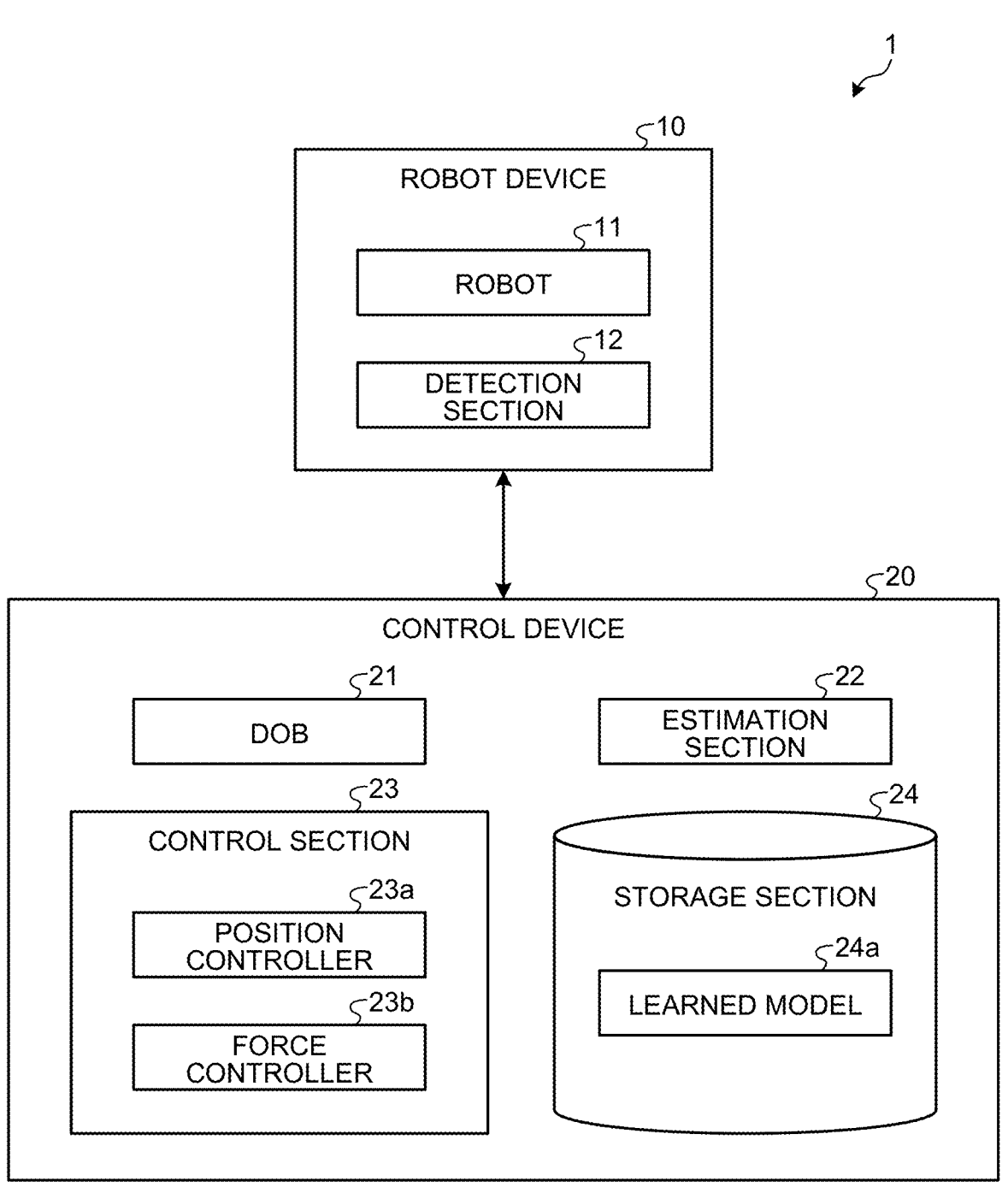
FIG. 1 is a diagram illustrating an example of a schematic configuration of a control system according to one embodiment.

A configuration example of a control system 1 according to one embodiment will be described with reference to FIG. 1. FIG. 1 is a view illustrating an example of a schematic configuration of the control system 1 according to the one embodiment.

As illustrated in FIG. 1, the control system 1 includes a robot device 10 and a control device 20. The robot device 10 includes a robot 11 and a detection section 12. The control device 20 includes a DOB 21, an estimation section 22, a control section 23, and a storage section 24.

The robot 11 is, for example, an arm device having a multi-link structure including an arm, a joint section, and the like. The robot 11 is, for example, a medical robot, but is not limited thereto, and may be an industrial robot. Details of the robot 11 will be described later.

The detection section 12 detects a state of the robot 11. Examples of the detected state include a torque reference value, an angle (joint angle), an angular velocity (joint angular velocity), and the like of a joint section. The torque reference value substantially corresponds to a current value input to the robot 11, and is detectable since being naturally grasped by the robot device 10. The angle of the joint section is acquired from, for example, an encoder in an actuator provided at the joint section of the robot 11. Details of the actuator will be described later. The angular velocity of the joint section is acquired by time-differentiation of the angle of the joint section. Other examples of the detected state are an acceleration reference value, position, speed, and the like of a distal end, these being input to the robot 11. The acceleration reference value is a value to be a base of the above-described torque reference value, and can be detected since being naturally grasped by the robot device 10 similarly to the torque reference value. The position of the distal end and the speed of the distal end can be detected since being specified from, for example, the angle, angular velocity, and the like of the joint section described above.

The DOB 21 is a disturbance observer that outputs a disturbance estimation value of the robot 11. For example, the DOB 21 outputs a disturbance estimation value of the joint section (magnitude of torque acting on the joint section) of the robot 11. Specifically, the DOB 21 outputs the disturbance estimation value of the joint section on the basis of the torque reference value, the angle, the angular velocity, and the like of the joint section.

The estimation section 22 estimates external force of the robot 11 (such as external force of a joint or a distal end of the robot 11) on the basis of state information of the robot 11. Here, the external force of the robot 11 is external force received by the robot, and the same applies hereinafter. The state information includes various kinds of information for specifying a state of the robot 11. Examples of the state information include the above-described torque reference value, angle, angular velocity, and the like. Other examples of the state information include the above-described acceleration reference value, position, speed, and the like. The state information may be, for example, time-series information indicating the state of the robot 11 for each time. Details of external force estimation by the estimation section 22 will be described later.

The control section 23 controls the robot 11 on the basis of an estimation result of the estimation section 22. The control by the control section 23 includes position control and force control. Functional blocks respectively corresponding to these kinds of control include a position controller 23a and a force controller 23b. The position controller 23a controls the robot 11 in such a manner that the position of the robot 11 becomes a desired position. The force controller 23b controls the robot 11 in such a manner that external force (torque or force) of the robot 11 becomes desired external force. Details of the external force control by the force controller 23b will be described later.

The position controller 23a controls the position of the robot 11 according to a value of a position command, for example. An example of a control position is a position of the distal end of the robot 11 (fingertip position). This control is performed in accordance with information designating the position of the distal end (fingertip position command). The position command such as the fingertip position command is generated according to user operation or generated by the control section 23. The position controller 23a controls, for example, a rotation (such as rotation speed, rotation angular velocity, and torque) of the joint section in such a manner that the distal end position of the robot 11 is located at a position corresponding to the fingertip position command.

The storage section 24 stores various kinds of information necessary for processing executed in the control device 20. For example, the storage section 24 stores a learned model 24a. The learned model 24a outputs a disturbance estimation value of when it is assumed that the robot 11 is in an unloaded state. The unloaded state of the robot 11 indicates a state in which the robot 11 is not in contact with other objects and the disturbance estimation value of the DOB 21 does not include the external force. Details of the learned model 24a will be described later.

<1-2. Configuration Example of a Robot>

Figure 2:
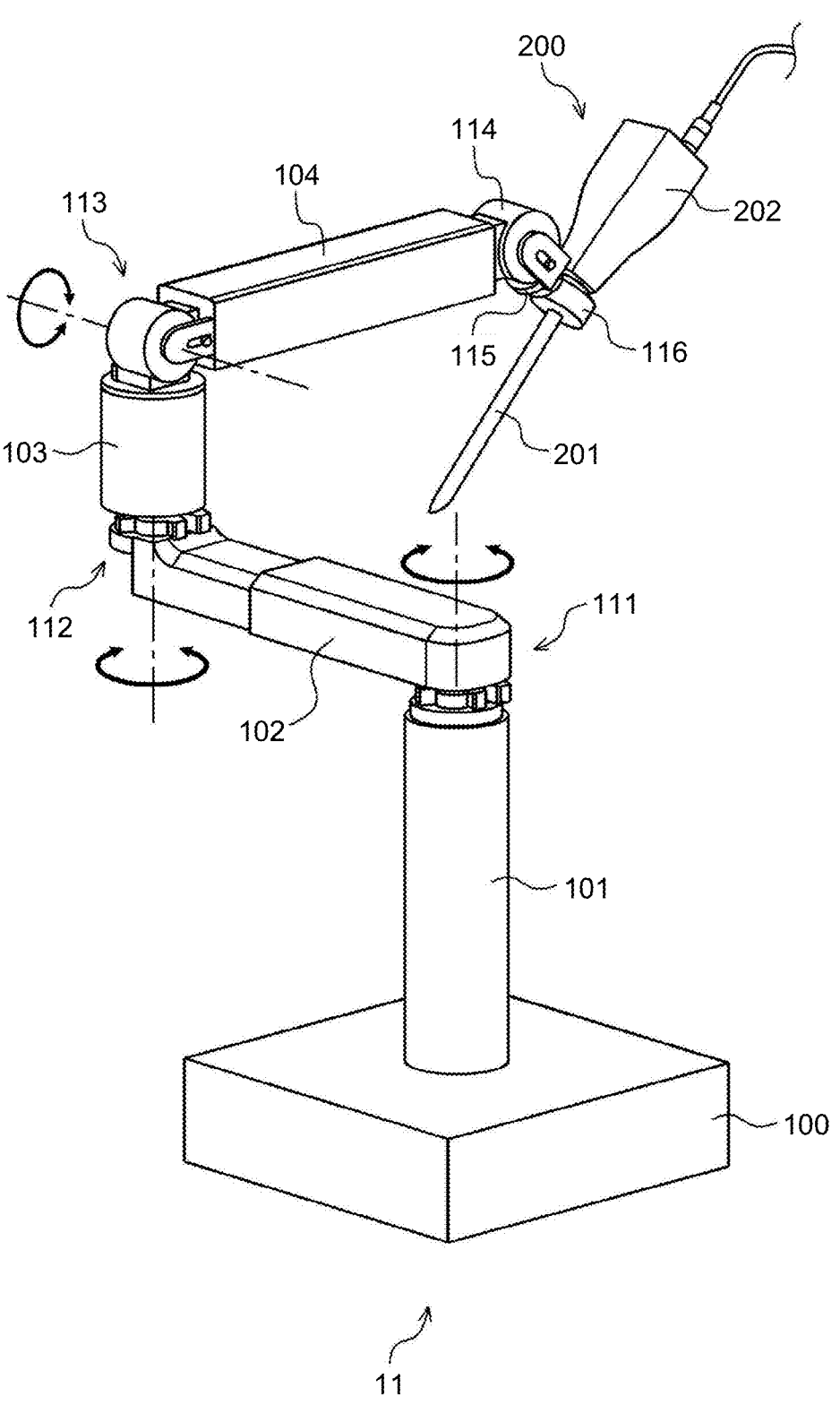
FIG. 2 is a diagram illustrating an example of a schematic configuration of a robot according to the one embodiment.

A configuration example of the robot 11 according to the one embodiment will be described with reference to FIG. 2. FIG. 2 is a diagram illustrating an example of a schematic configuration of the robot 11 according to the one embodiment.

As illustrated in FIG. 2, the robot 11 is, for example, a medical arm device. The robot 11 is an arm having a multi-link structure, supports an endoscope 200 by the distal end of the arm, and has a configuration in which orthogonal rotation axes of three degrees of freedom which axes determine a posture of the endoscope 200 are intensively arranged.

Specifically, the robot 11 includes a first link 101 attached substantially vertically to a base 100, a first joint section 111 having a degree of freedom around a horizontal rotation axis (or a longitudinal axis of the first link 101) at a distal end of the first link 101, a second link 102 attached in a horizontal direction to the distal end of the first link 101 via the first joint section 111, a second joint section 112 having a degree of freedom around a horizontal rotation axis (or an axis orthogonal to a longitudinal axis of the second link 102) at a distal end of the second link 102, a third link 103 attached substantially vertically to the distal end of the second link 102 via the second joint section 112, a third joint section 113 having a degree of freedom around a vertical rotation axis orthogonal to the horizontal rotation axis (or an axis orthogonal to a longitudinal axis of the third link 103) at a distal end of the third link 103, a fourth link 104 attached to a distal end of the third link 103 via the third joint section 113, and a distal end that supports the endoscope 200 at the distal end of the fourth link 104. Note that the base 100 may be attached to a frame of an operation bed, may be installed on a floor surface of an operating room, or may be installed on a ceiling, for example.

The distal end that supports the endoscope 200 at a distal end of the fourth link 104 has a structure in which orthogonal rotation axes of three degrees of freedom which axes determine a posture of the endoscope 200 are intensively arranged. The structure in which the orthogonal rotation axes of the three degrees of freedom are intensively arranged of the distal end corresponds to, for example, a structure in which three orthogonal rotation shafts are connected without a link, or a structure in which joint members corresponding to the three rotation axes are directly connected. More specifically, a member connecting the three joint sections is not a link that gains an arm length but only a component that connects the joint sections. Note that the fourth link 104 having the distal end that supports the endoscope 200 is assumed as a first arm. Furthermore, link sections (the first link 101 and the second link 102) including two horizontal rotation axes (the first joint section 111 and the second joint section 112) is assumed as a second arm. In the example of FIG. 2, the second arm is coupled by the third joint section 113 having the degree of freedom around the vertical rotation axis.

The endoscope 200 includes a lens barrel 201 inserted into a body cavity of a patient at a distal end, and a camera head 202 connected to a proximal end of the lens barrel 201. The lens barrel 201 may be either a rigid scope including a rigid lens barrel or a flexible scope including a flexible lens barrel. An optical system and an imaging element (both not illustrated) are arranged in the camera head 202. Reflected light (observation light) from an observation target such as a surgical site is imaged on the imaging element by the optical system. Obviously, the distal end of the robot 11 may support a medical instrument other than the endoscope 200.

The distal end of the robot 11 includes a vertical rotation shaft section 114 that has a degree of freedom around the vertical rotation axis (or axis orthogonal to the longitudinal axis of the fourth link 104) at the distal end of the fourth link 104 and that swings the endoscope 200 in a vertical direction, a right-left rotation shaft section 115 that is adjacent to the vertical rotation shaft section 114, that has a degree of freedom around a right-left rotation axis orthogonal to the vertical rotation axis, and that swings the endoscope 200 in a right-left direction, and an optical-axis rotation shaft section 116 that has a degree of freedom around an optical axis of the endoscope 200 (or the lens barrel 201 of the endoscope 200). Thus, the orthogonal rotation axes of the three degrees of freedom that determine the posture of the endoscope 200 have a structure in which the optical-axis rotation axis, the right-left rotation axis, and the vertical rotation axis of the endoscope 200 are arranged in this order from the most distal end.

Note that the right-left rotation shaft section 115 can be referred to as a pan axis that changes an observation direction of the endoscope 200, and the vertical rotation shaft section 114 can be referred to as a tilt axis. Alternatively, in a case where the optical-axis rotation shaft section 116 is a roll axis, the right-left rotation shaft section 115 can be referred to as a yaw axis, and the vertical rotation shaft section 114 can be referred to as a pitch axis. When the combined volume of the joint sections corresponding to these three axes is smaller than the combined volume of a wrist and a hand of a human, there is an advantage of using the robot 11 instead of the scopist. The optical-axis rotation shaft section 116 desirably minimizes a length to grip the endoscope 200 in the axial direction in such a manner as not to reduce an effective length of the endoscope 200. In addition, a distance between the vertical rotation shaft section 114 and the optical-axis rotation shaft section 116 is desirably set to a length that avoids self-interference of the arm.

The structure in which the orthogonal rotation axes of the three degrees of freedom are intensively arranged is a structure in which the joint members corresponding to the rotation axes of the three degrees of freedom are directly connected, or a structure in which a distance between the joint corresponding to the rotation axis around the axis in the longitudinal direction and the joint corresponding to the pitch axis has a distance that does not cause interference at the time of rotation around the pitch axis. Thus, it is possible to reduce a space affected by the movement of the distal end, and to control interference with a work space of an operator. Incidentally, in a case where the vertical rotation shaft section 114 is arranged closer to a base side, it is assumed that movement on a hand side of an operator becomes large when the vertical rotation shaft section 114 is operated.

<1-3. Configuration Example of an Actuator>

Figure 3:
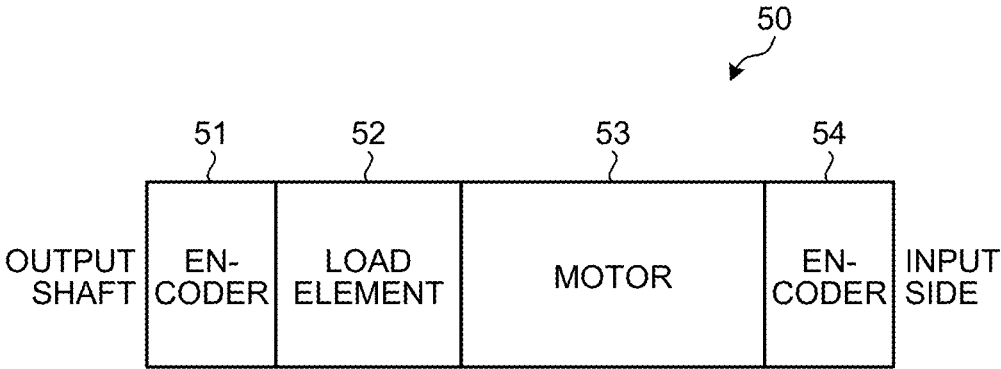
FIG. 3 is a diagram illustrating an example of a schematic configuration of an actuator according to the one embodiment.
Figure 4:
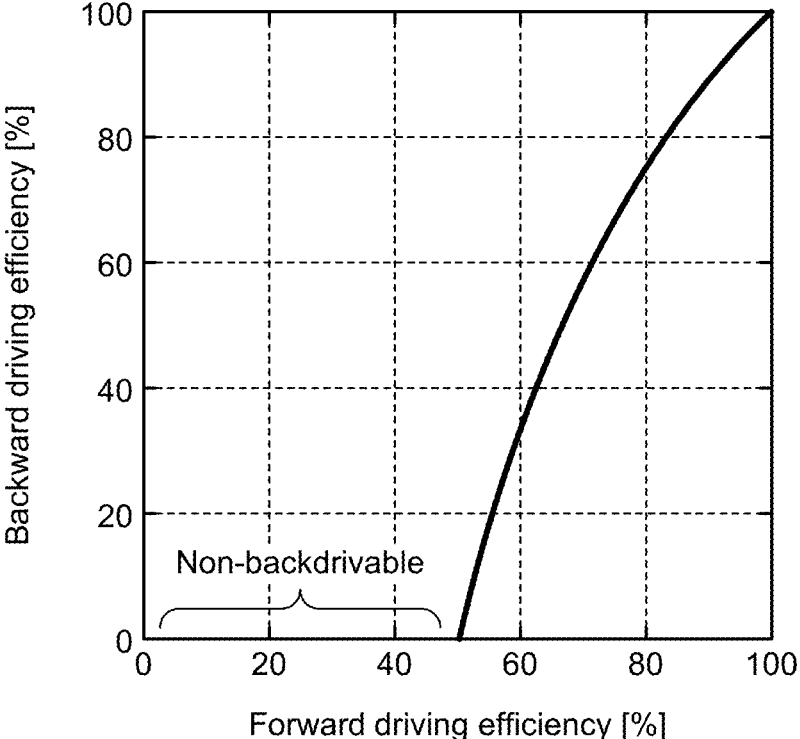
FIG. 4 is a diagram illustrating a relationship between forward driving efficiency and backward driving efficiency according to the one embodiment.
Figure 5:
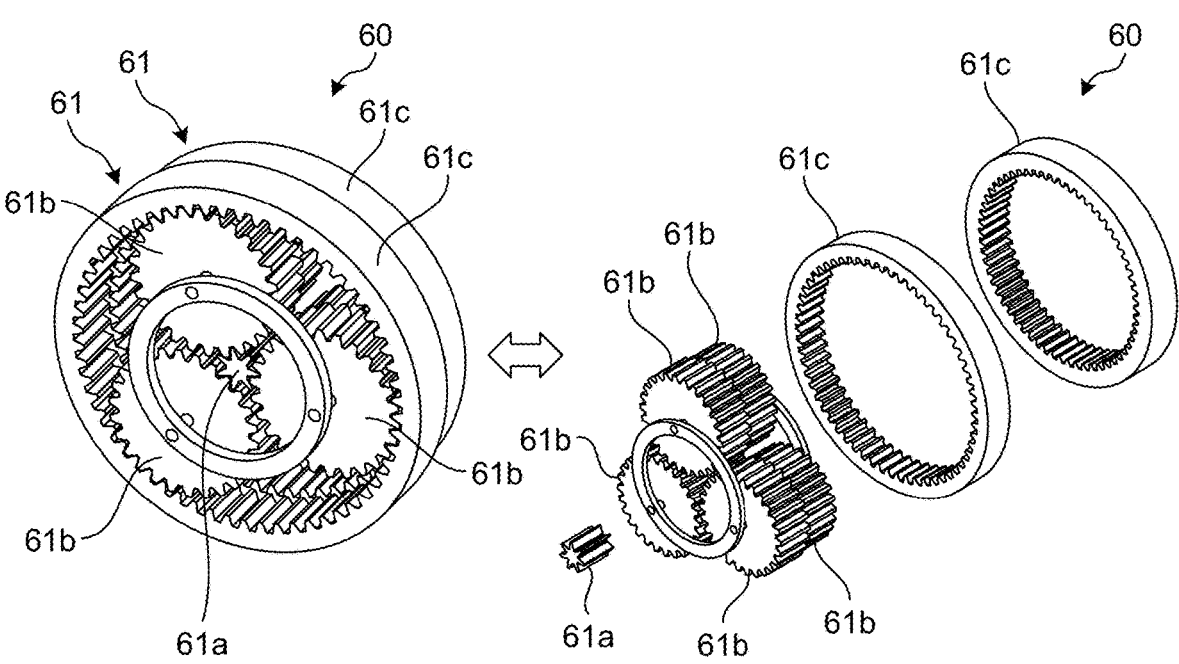
FIG. 5 is a diagram illustrating an example of a schematic configuration of a high-efficiency planetary speed reducer according to the one embodiment.
Figure 6:
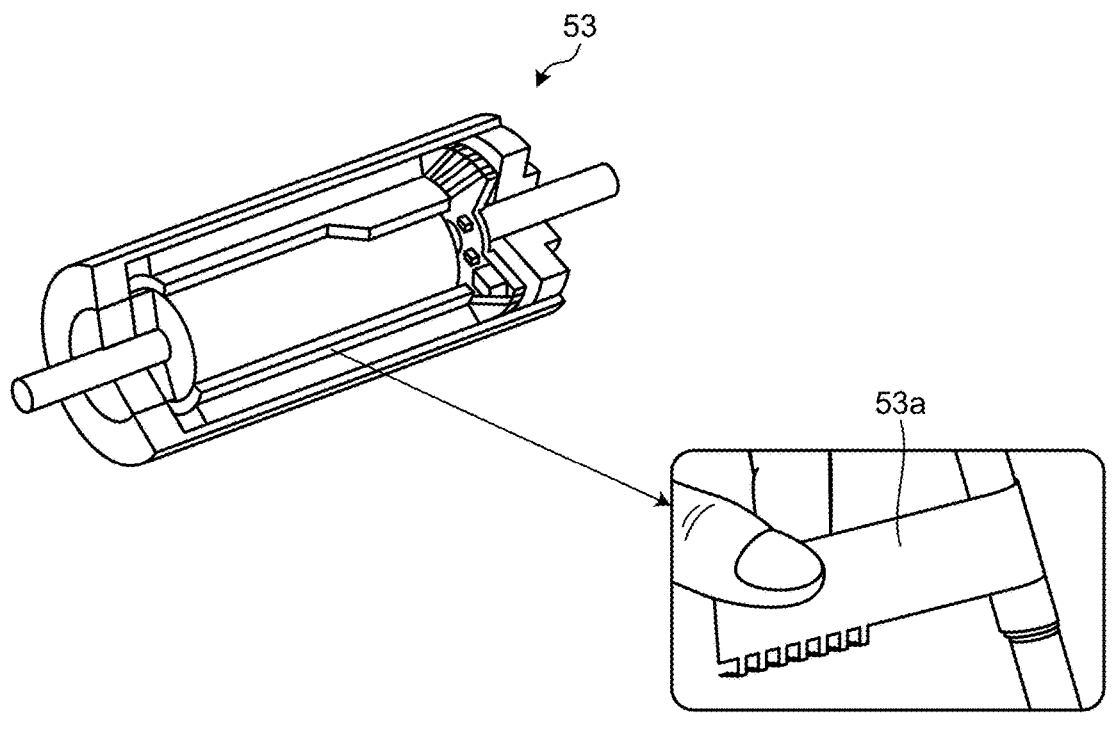
FIG. 6 is a diagram illustrating an example of a schematic configuration of a motor according to the one embodiment.
Figure 7:
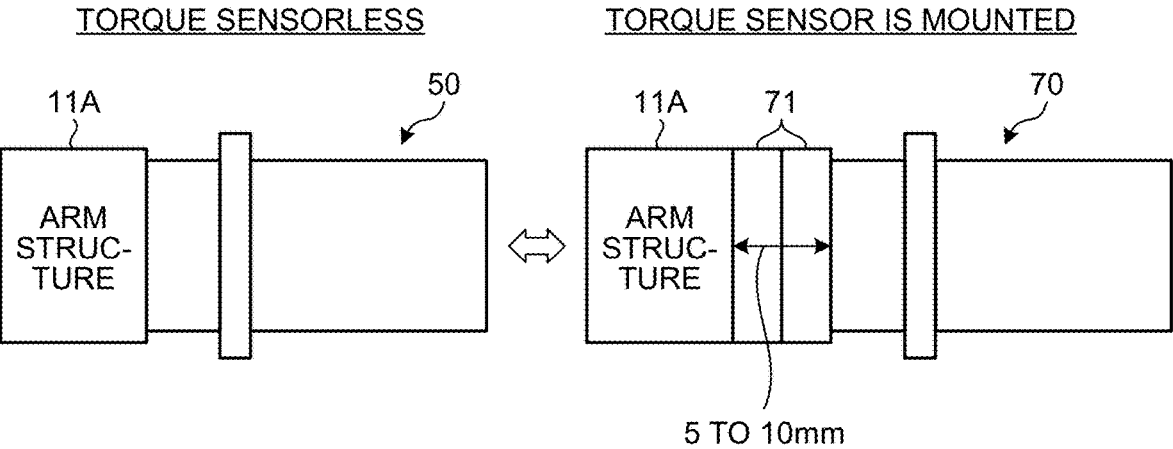
FIG. 7 is a diagram for describing a difference between the actuator according to the one embodiment and an actuator according to a comparative example.

A configuration example of an actuator 50 according to the one embodiment will be described with reference to FIG. 3 to FIG. 7. FIG. 3 is a diagram illustrating an example of a schematic configuration of the actuator 50 according to the one embodiment. FIG. 4 is a diagram illustrating a relationship between forward driving efficiency and backward driving efficiency according to the one embodiment. FIG. 5 is a diagram illustrating an example of a schematic configuration of a high-efficiency planetary speed reducer 60 according to the one embodiment. FIG. 6 is a diagram illustrating an example of a schematic configuration of a motor 53 according to the one embodiment. FIG. 7 is a diagram for describing a difference between the actuator 50 according to the one embodiment and an actuator 70 according to a comparative example.

As illustrated in FIG. 3, the actuator 50 includes an encoder 51, a load element 52, the motor 53, and an encoder 54 sequentially from an output shaft side to an input shaft side. The encoder 51, the load element 52, the motor 53, and the encoder 54 are coupled, whereby the actuator 50 is configured. In the example of FIG. 3, in the actuator 50, an encoder is mounted on each of an output shaft and an input shaft, that is, the encoder 51 is mounted on the output shaft side, and the encoder 54 is mounted on the input shaft side. Such an actuator 50 is, for example, an actuator module applied to any or all of the first joint section 111, the second joint section 112, the third joint section 113, the vertical rotation shaft section 114, the right-left rotation shaft section 115, the optical-axis rotation shaft section 116, and the like.

As each of the encoders 51 and 54, for example, a magnetic or optical rotary encoder is used. Note that it is better that accuracy of each encoder 54 is higher. A speed reducer is used as the load element 52. This speed reducer has, for example, an elastic component, and is located between the encoder 51 on the output shaft side and the motor 53. Note that a sensor or the like may be added as the load element 52 in addition to the speed reducer. As the motor 53, for example, an electromagnetic motor is used. However, there are no restrictions on a kind and a type of the motor.

As the speed reducer, a speed reducer capable of back driving, such as a speed reducer having backdrivability of flexibly moving with respect to external force is used. The forward driving is driving of being rotated by force from the motor 53, and the back driving is driving of being rotated by the external force from the output shaft side. In order to realize the back driving, for example, as illustrated in FIG. 4, a speed reducer having at least forward driving efficiency of 50% or more is mounted. In the example of FIG. 4, back driving of the speed reducer can be performed when the forward driving efficiency is 50% or more. For example, in order to reliably set backward driving efficiency to 20% or more, it is preferable to use a speed reducer having the forward driving efficiency of 60% or more. Furthermore, in order to reliably set the backward driving efficiency to 70% or more, it is preferable to use a speed reducer having the forward driving efficiency of 80% or more.

For example, as illustrated in FIG. 5, a high-efficiency planetary speed reducer (bilateral drive speed reducer) 60 is used as the speed reducer. The high-efficiency planetary speed reducer 60 has, for example, the same structure as a complex planetary speed reduction mechanism. The high-efficiency planetary speed reducer 60 has a structure in which planetary gear mechanisms 61 are coaxially overlapped in two stages. Each of the planetary gear mechanisms 61 includes a sun gear 61*a* that is a gear at a center of the mechanism, a plurality of planetary gears 61*b* that is revolving gears, and an internal gear 61*c* that is meshed with each of the planetary gears 61*b* and rotates. As a result, a high reduction ratio can be realized, and a low backlash and downsizing can be realized. The backlash is, for example, play between tooth surfaces. The forward driving efficiency of the high-efficiency planetary speed reducer 60 is, for example, 80% to 90% or more. In addition, the gears (such as the sun gear 61*a*, the planetary gears 61*b*, the internal gear 61*c*, and the like) may have coating layers that reduce friction on outer peripheral sections that mesh with each other. For example, coding processing is executed on the uneven outer peripheral section of each of the gears, and the coding layer is formed on the outer peripheral section.

Normally, a torque sensor needs to be arranged on an output side in order to control load torque of the speed reducer. However, in the high-efficiency planetary speed reducer 60, an actual measured value of load torque by an output-side torque sensor and an estimation value of load torque by a motor-side encoder accurately coincide with each other due to good backdrivability. Thus, for example, since it is possible to estimate and control the torque on the output side from the motor side, the torque sensor on the output side becomes unnecessary. In addition, heat at the time of braking by back driving may be efficiently recovered as electric energy. In this case, power consumption can also be reduced.

With respect to the motor 53, in a case of being rotated from the output shaft side of the actuator 50, a ripple component of the motor 53 is increased to a multiple of the reduction ratio. Thus, in order to maintain high reversibility as the actuator 50 in combination with a speed reduction mechanism having the high reduction ratio, it is preferable that cogging torque of the motor 53 is low or there is no cogging torque. Thus, for example, it is desirable to mount a motor having the cogging torque of 50% or less with respect to motor rated torque.

For example, as illustrated in FIG. 6, as the motor 53, a coreless motor in which a motor winding wire is realized by a flexible substrate 53*a* is used. A wiring line serving as the motor winding wire is printed on the flexible substrate 53*a*. As a result, since the motor 53 is the coreless motor, it is possible to realize elimination of cogging torque. In addition, since the motor winding wire is configured by the flexible substrate 53*a*, it is possible to achieve higher output than a motor using a normal wire rod.

According to the actuator 50 having the above configuration, since the actuator 50 is configured by mounting of the speed reducer having high reversibility (high backdrivability) as the load element 52 and mounting of the low cogging motor 53, it is possible to reduce a mechanical loss (friction and viscosity) at the time of back driving. That is, in order to realize highly accurate torque sensorless control, the actuator 50 in which the highly reversible speed reducer and the low cogging motor are combined can be configured.

For example, force control without the torque sensor can be realized by employment of the configuration of the actuator 50 in which a reversible speed reducer is mounted. In addition, by mounting the highly reversible speed reducer on the actuator 50, it possible to reduce reverse movable torque of the actuator 50, reduce a dead zone of control, and improve resolution of the torque control. By mounting the low-backlash speed reducer on the actuator 50, driving accuracy of the actuator 50 can be improved, and position control accuracy of the mounted robot 11 can be improved. By mounting the low cogging motor, it is possible to reduce the reverse movable torque of the actuator 50, reduce the dead zone of the control, and improve the resolution of the torque control even in combination with the speed reducer having the high speed reduction ratio. By combining the speed reducer having the high reduction ratio with a small and high-output motor, it is possible to improve output density of the actuator 50 and to realize the small and light robot 11.

in addition, as illustrated in FIG. 7, according to the torque sensorless actuator 50, an arm structure (robot structure) 11A is directly connected to the output shaft of the actuator 50 when the actuator 50 is mounted on the robot. On the other hand, in the actuator 70 on which a torque sensor is mounted, an arm structure 11A is connected to an output shaft of the actuator 70 via a coupling mechanism 71 when the actuator 70 is mounted on a robot. With the coupling mechanism 71, a separation distance between the arm structure A1 and the actuator 70 is, for example, 5 to 10 mm, which leads to an increase in size of the mechanism. In addition, the coupling mechanism 71 and the arm structure 11A are complicated for countermeasures against noise with respect to the torque sensor. In addition, structural looseness is generated due to the noise countermeasure structure, and the positional accuracy is deteriorated.

Thus, by using the torque sensorless (or force sensorless), that is, torque/force sensorless actuator 50, it is possible to directly connect the arm structure 11A to the output shaft of the actuator 50. As a result, looseness of the mechanism is not generated and the positional accuracy can be improved (high accuracy). In addition, a cost for an additional mechanism at the time of mounting of the sensor can be reduced (cost reduction). Furthermore, it is possible to realize space reduction for the additional mechanism at the time of mounting of the sensor (downsizing and weight reduction). By realizing torque/force sensorless force control, it is possible to realize a human cooperative robot having both high accuracy and safety at low cost. Note that the actuator 50 according to the one embodiment can be applied to a wide range of fields such as an industrial field and a medical field.

(Other Speed Reducer)

Note that other speed reducers may be used as the speed reducer. Examples of the other speed reducers having the forward driving efficiency of 60% or more and capable of realizing back driving include a strain wave gearing speed reducer (Harmonic Drive (registered trademark)), a traction speed reducer, and a cycloidal speed reducer. According to the strain wave gearing speed reducer, it is possible to realize high accuracy (non-backlash), high rigidity, downsizing, and a high reduction ratio. However, the back driving characteristic may have large hysteresis (low repetitive reproducibility). In addition, according to the traction speed reducer, high accuracy (non-backlash) and high efficiency can be realized. However, sliding is generated over time, and it may be difficult to acquire a high reduction ratio. According to the cycloidal speed reducer, it is possible to realize high accuracy (low backlash), high rigidity, and a high reduction ratio. However, downsizing may be difficult. As the speed reducer, for example, a speed reducer having a backlash lower than a predetermined value (such as 5 deg) and having no backlash is desirably used.

(Other Motor)

In addition, other motors may be used as the motor 53. Examples of the electromagnetic motor that can achieve low cogging torque, and small size and high output include a coreless motor and a cored motor that copes with low cogging. According to the coreless motor, since a core is not provided in a winding wire, cogging torque is hardly generated. However, output density tends to decrease as compared with a cored motor. According to the cored motor that copes with low cogging, it is easy to increase the output density as compared with the coreless motor. However, it may be difficult to eliminate (reduce) the cogging torque, and measures against the cogging torque and output efficiency are in trade-off. As an example of coping with the low cogging, for example, the number of poles of a magnet and the number of slots of a coil are optimized, and skew magnetization to the magnet and sufficient securing of a gap between the coil and the rotor are performed.

Note that the robot device 10 in which the actuator 50 in a manner described above is embedded is a human cooperative medical robot, but is not limited thereto, and may be a human cooperative industrial machine. In the example of FIG. 2, the robot device 10 is a robot arm that grips and controls the endoscope 200 instead of a doctor at the time of surgical endoscopic surgery, and is an application example to which the actuator 50 can be applied. Since the actuator 50 does not require mounting of a torque sensor, a degree of freedom in designing of the arm joint section (such as the first joint section 111, the second joint section 112, the third joint section 113, and the like) and the arm distal end (such as the vertical rotation shaft section 114, the right-left rotation shaft section 115, the optical-axis rotation shaft section 116, and the like) is high, and adaptability to the arm mechanism is high.

<1-4. Processing Example of the Control System>

Figure 8:
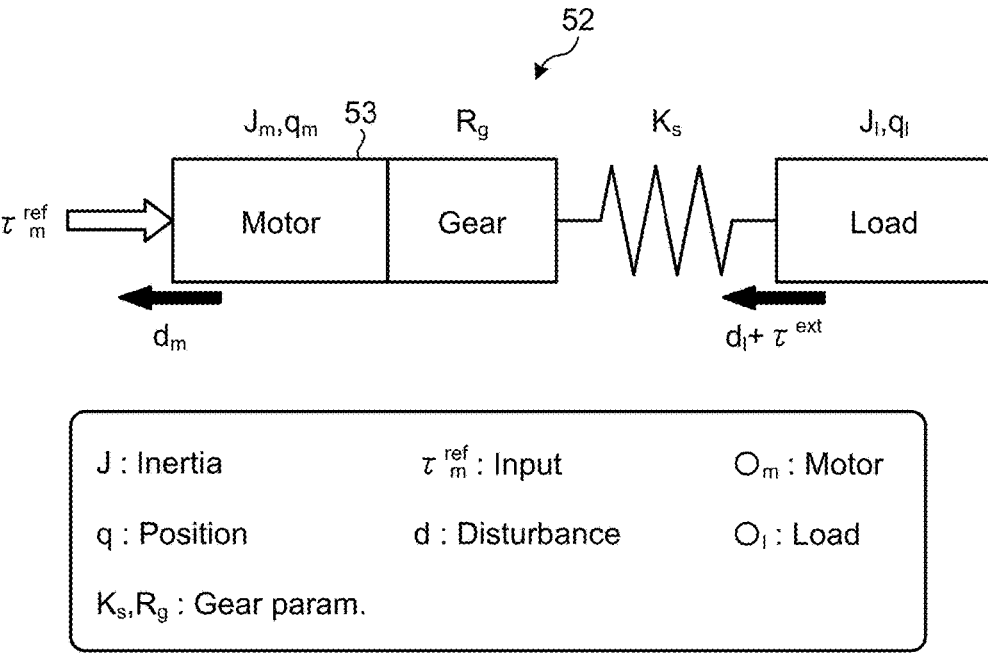
FIG. 8 is a diagram illustrating an example of a model of the motor and a speed reducer, which is a load element, according to the one embodiment.
Figure 9:
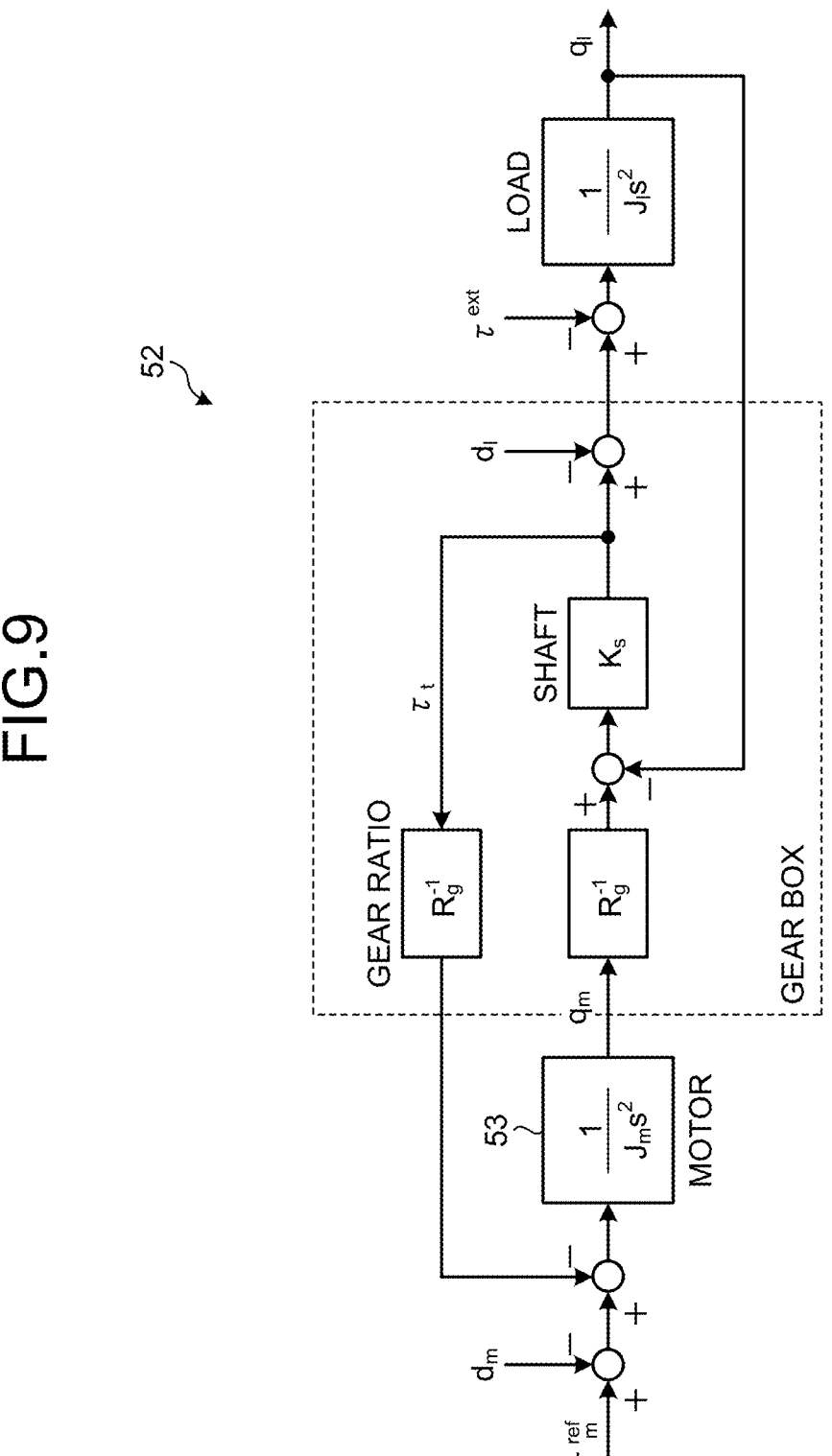
FIG. 9 is a diagram illustrating an example of a model of the motor and the speed reducer, which is the load element, according to the one embodiment.
Figure 10:
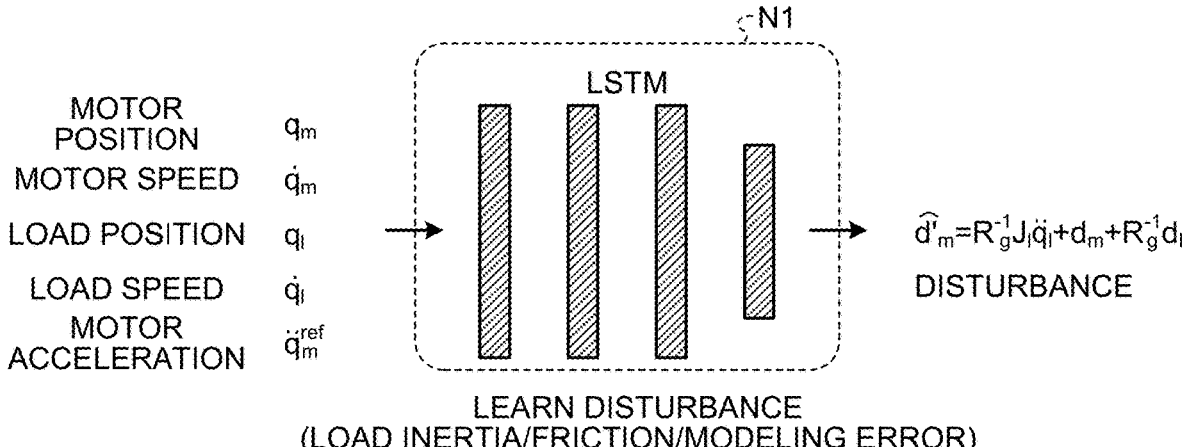
FIG. 10 is a diagram illustrating an example of a neural network according to the one embodiment.
Figure 11:
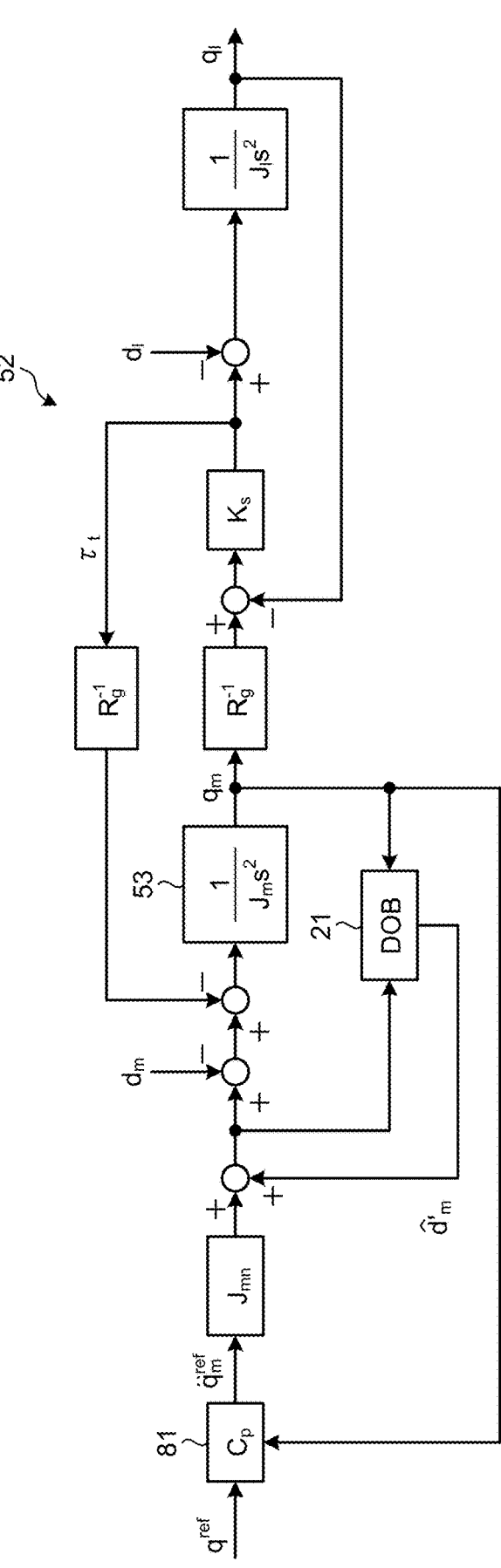
FIG. 11 is a diagram illustrating an example of a joint angle control system for acquiring learning data according to the one embodiment.
Figure 12:
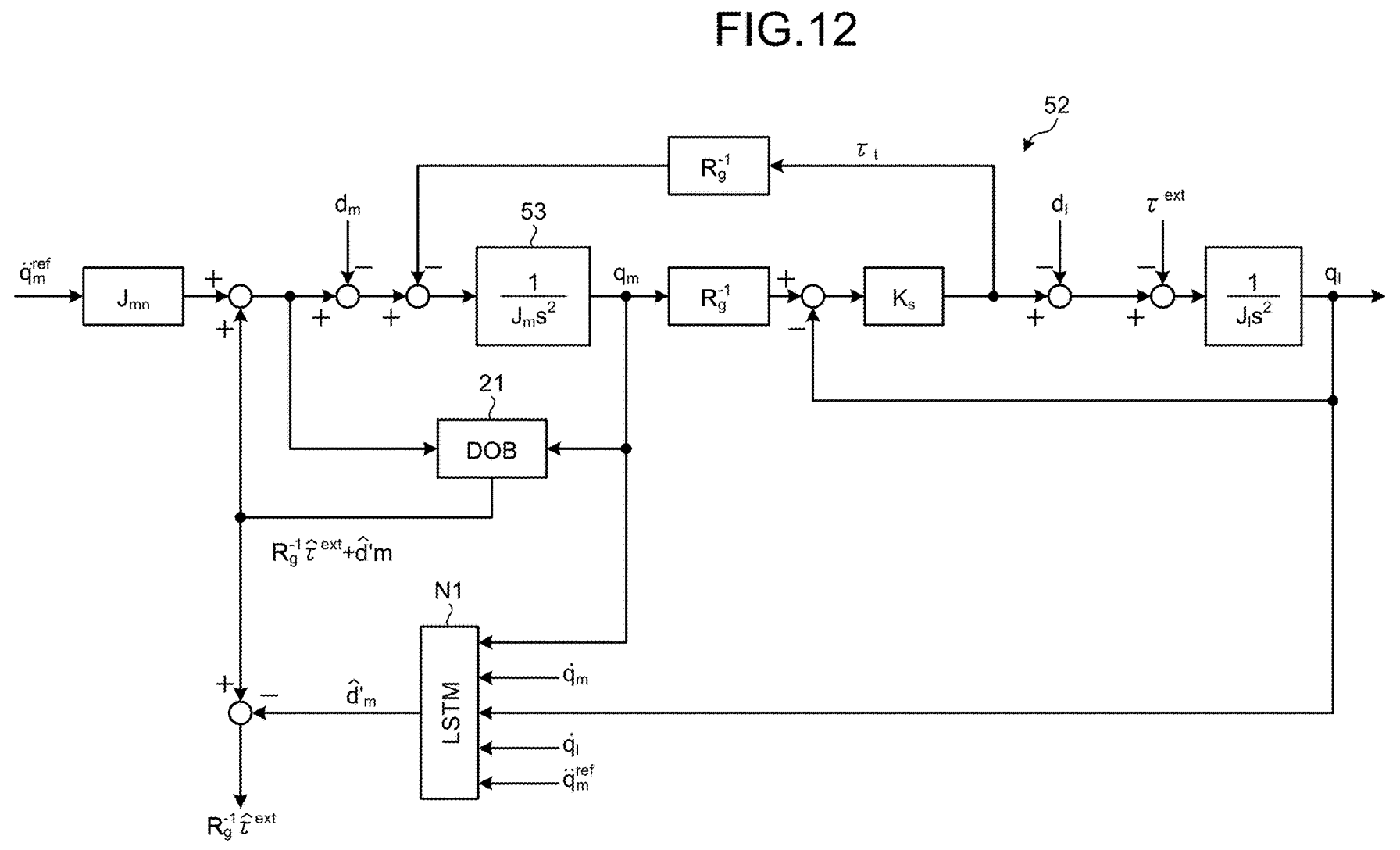
Figure 13:
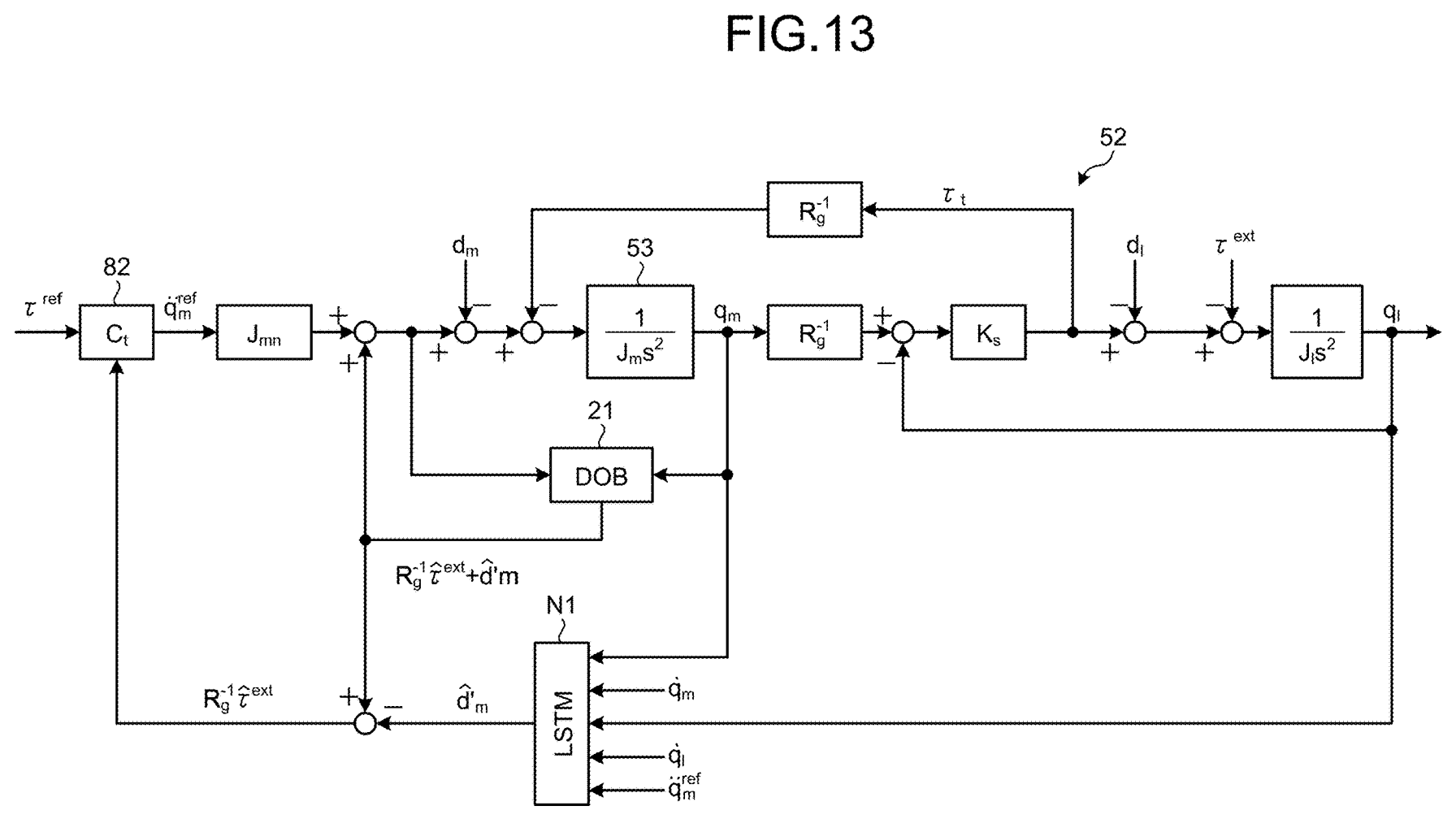
Figure 14:
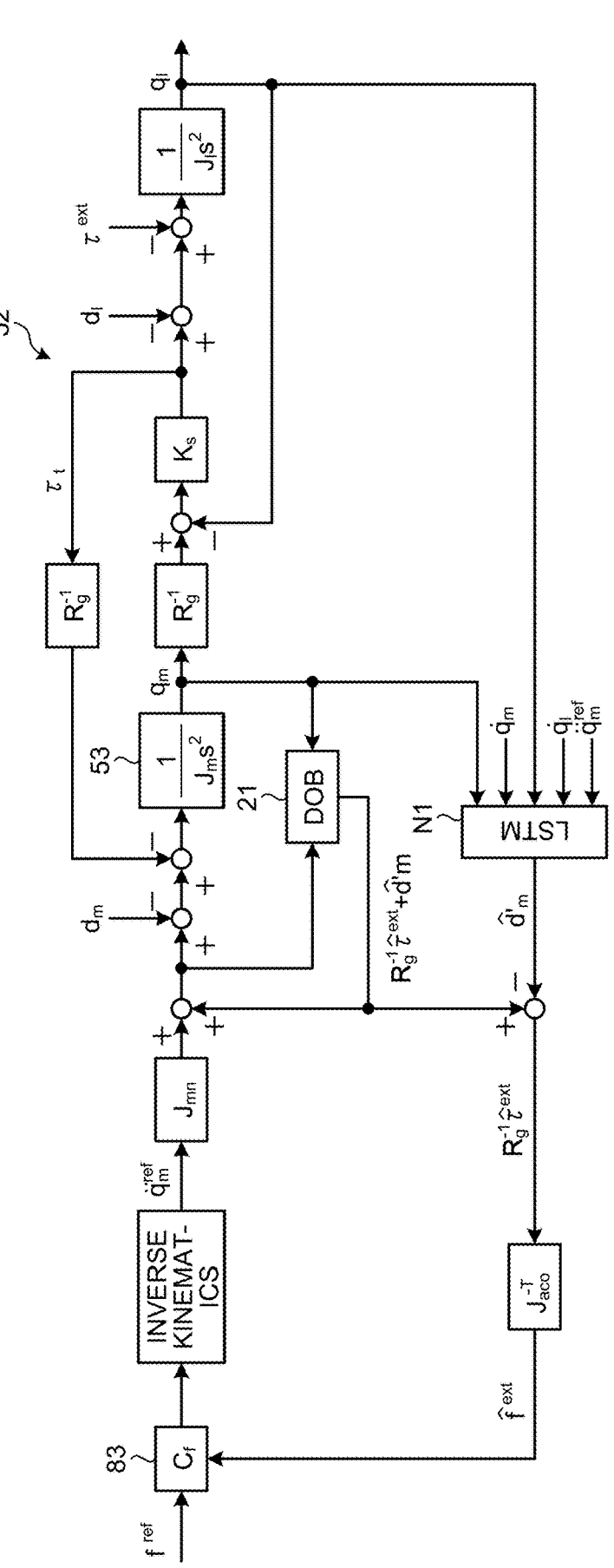
FIG. 14 is a diagram illustrating an example of a distal-end force control system according to the one embodiment.

A processing example of the control system 1 according to the one embodiment will be described with reference to FIG. 8 to FIG. 14. FIG. 8 to FIG. 14 are diagrams for describing the processing example of the control system 1 according to the one embodiment. Specifically, FIG. 8 and FIG. 9 are diagrams illustrating an example of a model of the motor 53 and the speed reducer (gear) that is the load element 52. FIG. 10 is a diagram illustrating an example of the neural network N1. FIG. 11 is a diagram illustrating an example of a joint angle control system for acquiring learning data. FIG. 12 is a diagram illustrating an example of an external torque estimator. FIG. 13 is a view illustrating an example of a torque control system. FIG. 14 is a view illustrating an example of a distal-end force control system.

Here, as described above, in the actuator 50, the encoders (the encoder 54 on the input shaft side and the encoder 51 on the output shaft side) are mounted on the input shaft and the output shaft in such a manner that the angle of the input/output shaft of each joint can be acquired. Furthermore, the control device 20 includes, for example, hardware (such as a personal computer or the like) having a real-time property.

In the present embodiment, as described above, first, the actuator 50 having the high back drive gear is mounted on each joint and low friction is realized. Then, the control system 1 randomly performs position control on the basis of the possible angle, angular velocity, and acceleration of each joint of the robot 11, and causes learning of the neural network with the angle, the angular velocity, and the acceleration reference value of the input/output shaft of each joint at that time as inputs of the neural network, and the disturbance estimation value estimated by the DOB 21 as an output. Then, the control system 1 employs the learned model 24a, inputs time-series data of the angle, the angular velocity, and the torque reference value of each joint to the learned model 24a (learned neural network) in real time, and estimates only a disturbance component of each joint at the current time. Only an external force component is extracted by subtraction of the estimated disturbance value output from the learned model 24a from the output of the DOB 21.

(Modeling)

As illustrated in FIG. 8 and FIG. 9, the model of the speed reducer (gear), which is the load element 52, and the motor 53 is used. Dynamic characteristics at this time are expressed by the following expressions (1) to (3).

$$J_m \ddot{q}_m = \tau_m^{ref} - R_g^{-1} \tau_t - d_m \qquad (1)$$

-continued $$J_l \ddot{q}_l = \tau_t - \tau^{ext} - d_l \qquad (2)$$

$$\tau_t = K_s \left( R_g^{-1} q_m - q_l \right) \qquad (3)$$

Here, J, q, $\tau_t$, $\tau^{ext}$, d, $R_g$, and $K_s$ are inertia, an angle, torsion torque, external torque, disturbance, a reduction ratio, and a spring constant of the speed reducer, respectively. Subscript characters m and l are respectively a motor and a load, and are expressed as a two-inertia system. Double dotted q is acceleration.

When the above expressions (1) to (3) are modified and integrated as a dynamic characteristic of only the motor 53, the following expression (4) is acquired.

$$J_m \ddot{q}_m = \tau_m^{ref} - R_g^{-1} \tau^{ext} - \left( R_g^{-1} J_l \ddot{q}_l + d_m + R_g^{-1} d_l \right) \qquad (4)$$

In the above equation (4), the third term on the right side can be regarded as disturbance applied to the motor 53. This term includes load inertia torque, and torque due to friction applied to the motor 53 and the load or a modeling error. By accurately identifying and removing this disturbance term in advance, it is possible to acquire the external torque expressed in the second term on the right side. However, it is generally difficult to accurately identify the disturbance term. Thus, in the present embodiment, the disturbance term is learned and estimated by the neural network.

Here, for example, modeling is performed with a geared motor as a two-inertia system. Dynamics expression can be made by the angle, angular velocity, and acceleration reference value on the motor side (input shaft) and the angle and angular velocity on the load side (output shaft). A function of estimating only the disturbance component, which is applied to the motor 53, by the neural network is acquired on the basis of the dynamics expression. Since the dynamics in which not only the input shaft but also the output shaft are considered is designed, the estimation function of the neural network is improved in accuracy.

(Design of the Neural Network)

A neural network N1 in a manner illustrated in FIG. 10 is used. The neural network N1 is a deep neural network in which a long short-term memory (LSTM) block suitable for time-series data and a fully connected layer are combined.

As an input of the neural network N1, time-series data of the acceleration reference value of the input shaft, the angle of the input/output shaft, and the angular velocity of the input/output shaft to each joint is used. In the example of FIG. 10, $q_m$ is a motor position (angle), and dotted $q_m$ is a motor speed (angular velocity). $q_l$ is a load position (angle) and dotted $q_l$ is a load speed (angular velocity). Double dotted $q_m^{ref}$ is a motor acceleration reference value.

Furthermore, as an output of the neural network N1, the following expression (5) is used as the third term on the right side of the above expression (4) (see FIG. 10).

$$\hat{d}_m = R_g^{-1} J_l \ddot{q}_l + d_m + R_g^{-1} d_l \qquad (5)$$

Disturbance of the above expression (5) includes torque due to friction of the speed reducer and a modeling error, that is, disturbance other than external force from an external environment or an operator (environmental reaction force).

As a result, the disturbance other than the external force is learned and estimated in each joint.

(Learning Method)

In order to acquire learning data, the learning data is acquired by angle control based on the DOB 21 illustrated in FIG. 11 in an unloaded state of the robot 11. In FIG. 11, $C_p$ is an angle controller 81, and $q^{ref}$ is an angle reference value. The angle controller 81 is included in the position controller 23a, for example. Here, the unloaded state is a state in which the robot 11 is not in contact with anything and the external torque is not included in the disturbance value estimated from the DOB 21. At this time, for example, the possible angle and angular velocity of each joint in a later inference phase are designed in advance, and the angle is controlled on the basis of the information.

The learning data is acquired in such a manner. The learned model 24a (learned neural network N1) is generated by utilization of the acquired learning data. The generation (learning) of the learned model 24a may be performed by the control device 20 or may be performed outside the control system 1 (such as an information processing device or the like). The generated learned model 24a is stored in the storage section 24 of the control device 20.

(Implementation Method of the External Torque Estimator)

By utilization of the estimation value acquired by the neural network N1, an external force estimation value of each joint is derived as the following expression (6).

$$R_g^{-1} \tau^{ext} = \hat{\tau}^{dob} - \hat{d}_m \qquad (6)$$

In the above expression (6), $\tau^{dob}$ with a hat is the disturbance estimation value output from the DOB 21, and includes external torque (reaction torque) from the operator and the external environment in addition to the disturbance such as friction at the time of external torque estimation. On the other hand, $d_m$ with a hat output from the learned neural network N1 is acquired by estimation of only the disturbance other than the external force, such as friction as described above. Thus, it is possible to extract only an external torque component of each joint by performing subtraction as in the above expression (6).

For example, the external torque estimator in a manner illustrated in FIG. 12 is acquired. As illustrated in FIG. 12, the disturbance estimation value ($R_g^{-1}\tau^{ext}+d_m$ with a hat$=\tau^{dob}$ with a hat) estimated from the DOB 21 includes (external torque+disturbance other than the external torque). Thus, by subtracting the value ($d_m$ with a hat) estimated by the learned neural network N1 from the disturbance estimation value estimated from the DOB 21, it is possible to calculate the external force ($R_g^{-1}\tau^{ext}$). That is, an external torque estimation value can be calculated from the expression (external torque+disturbance other than the external torque)−(estimation value of disturbance other than the external torque)=the external torque estimation value.

The external torque estimator is included in the estimation section 22, for example. That is, the estimation section 22 estimates the external force (such as external torque) of the robot 11 by subtracting the disturbance estimation value (value estimated by the learned neural network N1) of when the robot 11 is assumed to be in the unloaded state from the disturbance estimation value of the DOB 21 of the robot 11 (disturbance estimation value of when the robot 11 is in the loaded state). That is, the estimation section 22 can acquire the external force estimation value of the robot joint and the external force estimation value of the robot distal end.

(Torque Control)

As illustrated in FIG. 13, a sensorless torque control system can be configured by utilization of the external force estimation value of the robot joint (each joint). In FIG. 13, Ct is a torque controller 82, and $\tau^{ref}$ is a torque reference value. The torque controller 82 is included in the force controller 23b, for example. By feeding back the external torque estimation value to the torque controller 82, it is possible to generate arbitrary torque in each joint.

(Robot Distal End Force Control)

As illustrated in FIG. 14, a sensorless robot distal-end force control system can be configured by utilization of the external force estimation value of the distal end of the robot. In FIG. 14, $C_f$ is a force controller 83, and $f^{ref}$ is a force reference value. The force controller 83 is included in the force controller 23b, for example. By feeding back the external force estimation value of the distal end of the robot to the force controller 83, it is possible to generate arbitrary force at the distal end of the robot.

Here, as inverse kinematics, by multiplying the external torque estimation value of the joint by an inverse transpose of a Jacobian matrix, it is possible to acquire the external force estimation value of the distal end of the robot in a manner of the following expression (7).

$$\hat{f}^{ext} = J_{aco}^{-T} R_g \hat{\tau}^{ext} \qquad (7)$$

(Conclusion)

According to the embodiment described above, since the actuator 50 is configured by mounting of the speed reducer having a high reversibility (high backdrivability) as the load element 52 and by mounting of the low cogging motor 53, a mechanical loss (friction and viscosity) at the time of back driving can be reduced, the control system 1 can function, and force/torque sensorless force control with high resolution can be realized.

Specifically, with respect to the speed reducer, when the external force is applied to the actuator 50, back driving of the speed reducer can be performed. Thus, the control system 1 can function and the force/torque sensorless force control can be realized. In addition, when the speed reducer having the forward driving efficiency of 50% or more is used, the inverse starting torque can be reduced. Thus, by combination of the control system 1, it is possible to realize force/torque sensorless force control with high resolution. When a speed reducer having the forward driving efficiency of 60% and having low backlash is used, force/torque sensorless force control and highly accurate position control can be realized.

In addition, since the motor 53 is equipped with the low cogging motor, back driving of the actuator 50 can be performed even when the reduction ratio is set high, the control system 1 can function, and the force/torque sensorless force control can be realized. Note that since the high-accuracy external torque estimation and torque control can be configured without the force/torque sensor, there is no cost or mechanical restriction of the force/torque sensor.

For example, in the force sensorless method, highly accurate identification like a white box is required. However, in general, this is difficult, and an error is always generated. Thus, application is not performed with respect to an application that requires highly accurate force detection, such as a medical instrument. For example, it is very difficult to model mechanical friction, and a modeling error remains. In the present embodiment, the function can be acquired with high accuracy in a black box manner by machine learning without requiring the above. For example, the accuracy can be improved by adapting of a learning technique to the estimation of the friction term that is difficult to be modeled. In addition, in order to realize accuracy improvement, for example, it is desirable to use a low cogging (small ripple) motor in addition to a speed reducer having high backdrivability.

Note that the configuration and the control according to the present embodiment are for a medical robot. However, other applications include the following. For example, the configuration and the control according to the present embodiment may also be applied to a cooperative robot or a leg robot. In a case where the configuration and the control are applied to the cooperative robot, it is possible to make a human cooperative system, which is conventionally realized by a force sensor, force sensorless. In addition, in a case where the configuration and the control are applied to the leg robot, a landing determination system conventionally realized by a sole force sensor can be made without a sole sensor.

<1-5. Action and Effect>

As described above, according to the one embodiment, the control system 1 includes the robot 11 including the actuator 50, and the estimation section 22 that estimates the external force of the robot 11 (external force received by the robot) on the basis of the state information of the robot 11, and the actuator 50 includes the encoder 51 on the output shaft side, the speed reducer (such as the high-efficiency planetary speed reducer 60) that is coupled to the encoder 51 on the output shaft side, that has backdrivability, and that is the load element 52, the motor 53 coupled to the speed reducer, and the encoder 54 on the input shaft side which encoder is coupled to the motor 53. As a result, since the actuator 50 is configured by mounting of the backdriving speed reducer as the load element 52, a mechanical loss (friction and viscosity) at the time of back driving can be reduced. In addition, the control system 1 can function and appropriately estimate the external force of the robot 11 without using the torque sensor or the force sensor.

Furthermore, the estimation section 22 may estimate the external force of the robot 11 by subtracting the disturbance estimation value of when it is assumed that the robot 11 is in the unloaded state from the disturbance estimation value of when the robot 11 is in the loaded state. As a result, the external force of the robot 11 can be accurately estimated.

Furthermore, the disturbance estimation value of when the robot 11 is in the loaded state may be the disturbance estimation value of the DOB 21 that is the disturbance observer. As a result, the external force of the robot 11 can be accurately estimated.

Furthermore, the estimation section 22 may acquire the disturbance estimation value of when it is assumed that the robot 11 is in the unloaded state by using the learned model 24a, and the learned model 24a may output, when the state information of the robot 11 is input, the disturbance estimation value of when it is assumed that the robot 11 is in the unloaded state. As a result, it is possible to estimate the external force of the robot 11 with high accuracy by using the learned model 24a acquired in a black box manner by machine learning.

Furthermore, the learned model 24a may include the long short-term memory (LSTM) block, and the state information of the robot 11 may be time-series information. As a result, for example, estimation accuracy of the disturbance can be improved as compared with a case where a multilayer perceptron is used.

Furthermore, the learned model 24a may be a model acquired by an input of time-series information of the acceleration reference value of the input shaft and the angle and the angular velocity of the input/output shaft to the neural network N1. As a result, the estimation accuracy of the disturbance can be improved.

Furthermore, the estimation section 22 may estimate external force of the joint section (such as the first joint section 111, the second joint section 112, the third joint section 113, and the like) or the distal end (such as the vertical rotation shaft section 114, the right-left rotation shaft section 115, the optical-axis rotation shaft section 116, and the like) of the robot 11. As a result, external force of the joint section or the distal end of the robot 11 can be appropriately estimated.

Furthermore, the robot 11 may include the joint section having the actuator 50, the state information of the robot 11 may include the torque reference value, the angle, and the angular velocity of the joint section, and the estimation section 22 may estimate external force of the joint section (external force received by the joint section). As a result, the estimation section 22 can estimate the external force of the joint section of the robot 11 on the basis of state information of the robot 11 which information includes the torque reference value, the angle, and the angular velocity of the joint section, whereby the external force of the joint section of the robot 11 can be accurately estimated.

Furthermore, the robot 11 may include the distal end having the actuator 50, the state information of the robot 11 may include the acceleration reference value, the position, and the speed of the distal end, and the estimation section 22 may estimate the external force of the distal end (external force received by the distal end). As a result, the estimation section 22 can estimate the external force of the distal end of the robot 11 on the basis of the state information of the robot 11 which information includes the acceleration reference value, the position, and the speed of the distal end, whereby the external force of the distal end of the robot 11 can be accurately estimated.

Furthermore, the robot 11 may include an arm (such as the arm part). Even in a case where the robot 11 includes the arm, the external force of the robot 11 can be appropriately estimated.

In addition, the speed reducer may be the speed reducer having the forward driving efficiency of 60% or more. As a result, back driving of the speed reducer can be performed, and the control system 1 can function appropriately.

In addition, the speed reducer may be the speed reducer having the backlash lower than the predetermined value (such as 5 deg). As a result, looseness of the mechanism can be controlled, and positional accuracy can be improved.

In addition, the speed reducer may be the speed reducer without backlash. As a result, looseness of the mechanism can be controlled, and positional accuracy can be improved.

In addition, the speed reducer (such as the high-efficiency planetary speed reducer 60) may include the plurality of gears (such as the sun gear 61a, the planetary gears 61b, the internal gear 61c, and the like), and the plurality of gears may have coating layers that reduce friction on the outer peripheral sections that mesh with each other. As a result, looseness of the mechanism can be controlled by control of friction between the gears, and positional accuracy can be improved.

In addition, the motor 53 may be the motor having the cogging torque of 50% or less with respect to the motor rated torque. As a result, even when the motor 53 is combined with the speed reducer having the high reduction ratio, it is possible to secure reverse possibility of the actuator 50, and the control system 1 can function appropriately.

Furthermore, the motor 53 may be the motor in which the winding wire is configured by the flexible substrate 53a. As a result, the output of the motor 53 can be improved, and the actuator 50 can be downsized.

Furthermore, the robot 11 may be the robot that holds an endoscope (such as a scopist robot). Even in a case where the robot 11 is the robot that holds the endoscope, the external force of the robot 11 can be appropriately estimated.

In addition, the speed reducer may be the speed reducer having the forward driving efficiency of 80% or more. This makes it possible to achieve both the force/torque sensorless force control and highly accurate position accuracy.

Furthermore, the motor 53 may be the coreless motor without the cogging torque. As a result, even when the motor 53 is combined with the speed reducer having the high reduction ratio, it is possible to secure the backdrivability of the actuator 50, and the control system 1 can function appropriately.

2. Other Embodiments

The processing according to the above-described embodiments (or modification examples) may be performed in various different forms (modification examples) other than the above-described embodiments. For example, the processing procedures, specific names, and information including various kinds of data or parameters in the above document or in the drawings can be arbitrarily changed unless otherwise specified. For example, various kinds of information illustrated in each of the drawings are not limited to the illustrated information. Also, the above-described embodiments (or modification examples) can be arbitrarily combined in a range in which the processing contents do not contradict with each other. Note that the effects described in the present specification are merely illustrative or exemplary, and are not limitations.

Also, each component of each of the illustrated devices is a functional concept, and does not need to be physically configured in the illustrated manner. That is, a specific form of distribution/integration of each device is not limited to what is illustrated in the drawings, and a whole or part thereof can be functionally or physically distributed/integrated in an arbitrary unit according to various loads and usage conditions.

Also, the above-described embodiments (or modification examples) can be arbitrarily combined in a range in which the processing contents do not contradict with each other. Also, the effect described in the present description is merely an example and is not a limitation, and there may be another effect.

Figure 15:
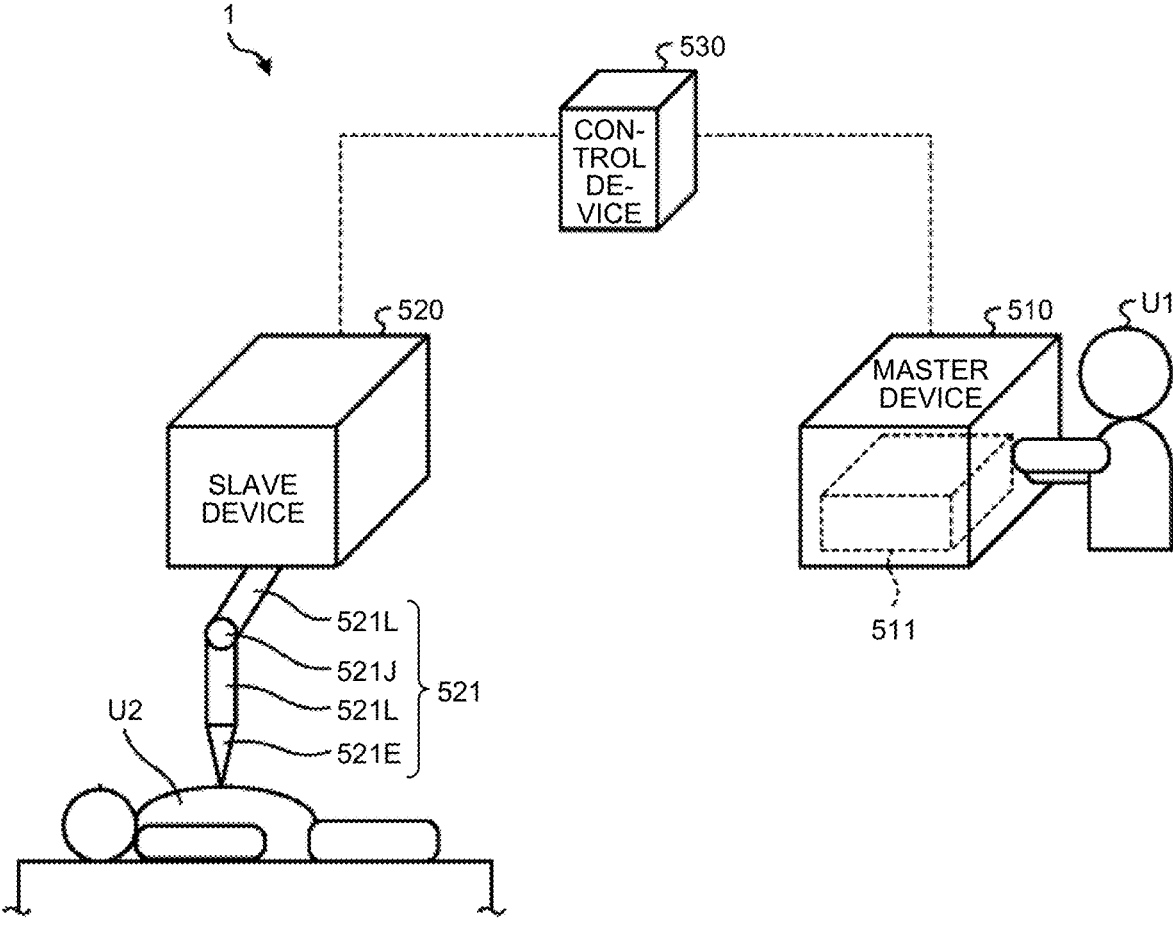
FIG. 15 is a diagram illustrating an example of a schematic configuration of a control system according to another embodiment.

For example, the control system 1 can be applied to a master-slave type control system. FIG. 15 is a diagram illustrating an example of a schematic configuration of a control system 1 according to another embodiment. The control system 1 is a master-slave type control system, and includes a master device 510, a slave device 520, and a control device 530. As schematically indicated by broken lines, the control device 530 is communicably connected to each of the master device 510 and the slave device 520. Information (such as data) used or acquired by each device is transmitted and received as necessary. Note that the communication may be performed via a network. Each of the devices may be connected to the network. In this case, the master device 510 and the slave device 520 may be directly connected to each other via the network.

In the example of FIG. 15, the control system 1 is used for surgery. An operator (such as a doctor) who performs an operation is referred to as a user U1 in the drawing. A patient undergoing the operation is referred to as a user U2 in the drawing. Each of the master device 510 and the slave device 520 corresponds to the robot device 10 illustrated in FIG. 1. In addition, the control device 530 corresponds to the control device 20 illustrated in FIG. 1.

The user U1 gives the operation on the user U2 by operating the master device 510 and remotely operating the slave device 520. Specifically, the master device 510 includes a master robot 511 operated by the user U1. The slave device 520 includes a slave robot 521 remotely controlled by the user U1. For convenience, the slave robot 521 and the master robot 511 will be described in this order. The slave robot 521 corresponds to the robot 11 illustrated in FIG. 2.

In this example, the slave robot 521 includes an arm. The slave robot 521 illustrated as an example includes link sections 521L, a joint section 521J, and a distal end 521E. The adjacent link sections 521L are rotatably connected via the joint section 521J that is rotated by motor driving. The distal end 521E is a section that is located the closest to the user U2 and that may come into contact with the user U2. The slave robot 521 has various states depending on, for example, a rotation angle or the like of the joint section 521J. Note that the slave robot 521 may include more link sections 521L, joint sections 521J, and distal ends 521E than those illustrated in the drawing. For example, an actuator 50 is applied to each of the joint sections 521J, the distal ends 521E, and the like. The following description related to the link sections, the joint sections, and the distal ends may be appropriately read as that of each of the link sections, each of the joint sections, and each of the distal ends.

The master robot 511 has a configuration suitable for the user U1 to remotely operate the slave robot 521. The operation (user operation) of the master robot 511 by the user U1 is transmitted as control information from the master device 510 to the slave device 520. I addition, the master robot 511 has a configuration corresponding to the slave robot 521 in such a manner as to transmit a state of the slave robot 521 to the user U1. The master robot 511 includes sections respectively corresponding to sections of the slave robot 521 in such a manner as to have states corresponding to the states of the respective sections (such as the link section 521L, the joint section 521J, and the distal end 521E) of the slave robot 521. The master robot 511 may include an arm similar to that of the slave robot 521. The user U1 can recognize the state of the slave robot 521, such as external force via the master robot 511. In the following, in the master robot 511, a section corresponding to the joint section 521J of the slave robot 521 is referred to as a "joint section of the master robot 511". In the master robot 511, a section corresponding to the distal end 521E of the slave robot 521 is referred to as a "distal end of the master robot 511".

One of the states of the slave robot 521 which states are transmitted to the user U1 is the external force of the slave robot 521. Specifically, it is important to transmit, to the user U1, the external force of the distal end 521E located the closest to the user U2 in the slave robot 521. Although it is conceivable to provide a force sensor (such as inner force sensor) in order to detect the external force of the distal end 521E (reaction force acting on the distal end 521E), a cost is necessary. In addition, there are many cases where there is no space for providing the force sensor in the first place. In the present embodiment, according to the above-described principle, the external force of the distal end 521E is appropriately estimated without utilization of the force sensor (in a force sensorless manner). Furthermore, similarly, the external force of the joint section 521J is appropriately estimated without utilization of a torque sensor (in a torque sensorless manner).

The control device 530 estimates the external force of the master robot 511 (such as the distal end) on the basis of state information of the master robot 511. In addition, the control device 530 estimates the external force of the slave robot 521 (such as the distal end 521E) on the basis of state information on the slave robot 521. Then, the control device 530 controls the master robot 511 and the slave robot 521 on the basis of an estimation result of the external force estimation. The control by the control device 530 includes position control and force control. Functional blocks respectively corresponding to these pieces of control include a position controller and a force controller. Since the control device 530 corresponds to the control device 20 illustrated in FIG. 1, the external force estimation is similar to the above principle.

The position controller of the control device 530 controls the master robot 511 and the slave robot 521 in such a manner that a position of the master robot 511 and a position of the slave robot 521 correspond to each other. The correspondence in the positions here means that positions of the corresponding sections of the master robot 511 and the slave robot 521 have a correspondence relationship. For example, the master robot 511 and the slave robot 521 are controlled in such a manner that the position of the distal end of the master robot 511 and the position of the distal end 521E of the slave robot 521 become the positions having a correspondence relationship.

The force controller of the control device 530 controls the master robot 511 and the slave robot 521 in such a manner that the external force of the master robot 511 and the external force of the slave robot 521 correspond to each other. The correspondence of the external force here means that the external force of the corresponding sections of the master robot 511 and the slave robot 521 have a correspondence relationship. For example, the master robot 511 and the slave robot 521 are controlled in such a manner that the external force of the distal end of the master robot 511 and the external force of the distal end 521E of the slave robot 521 become the external force having a correspondence relationship.

Also in such a master-slave type control system 1, by applying the technology according to the present disclosure to the master-slave type control system 1, it is possible to appropriately estimate the external force without using a torque sensor or a force sensor.

3. Application Example

The technology according to the present disclosure can be applied to a medical imaging system. The medical imaging system is a medical system using an imaging technology, and is, for example, an endoscope system or a microscope system.

[Endoscope System]

Figure 16:
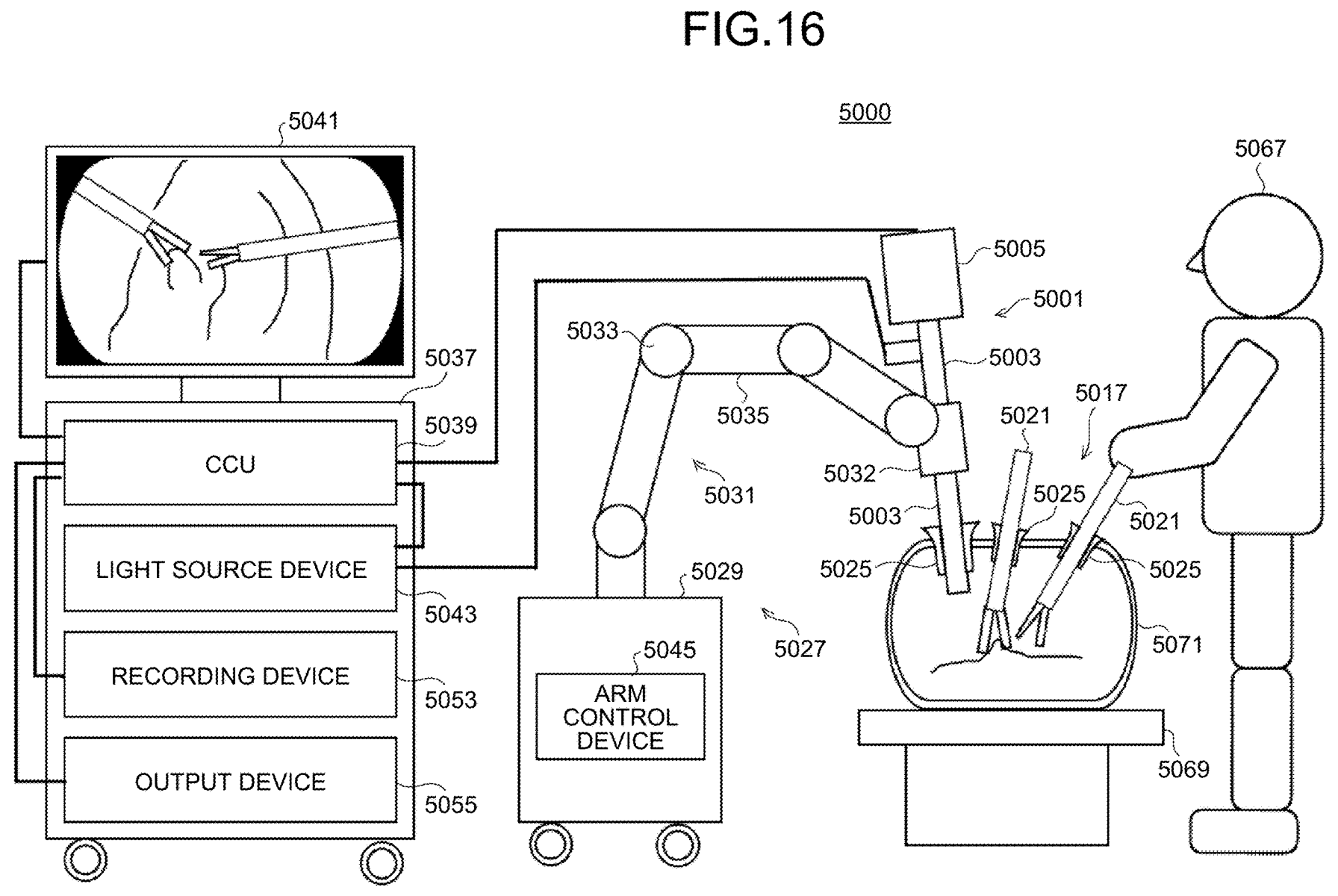
Figure 17:
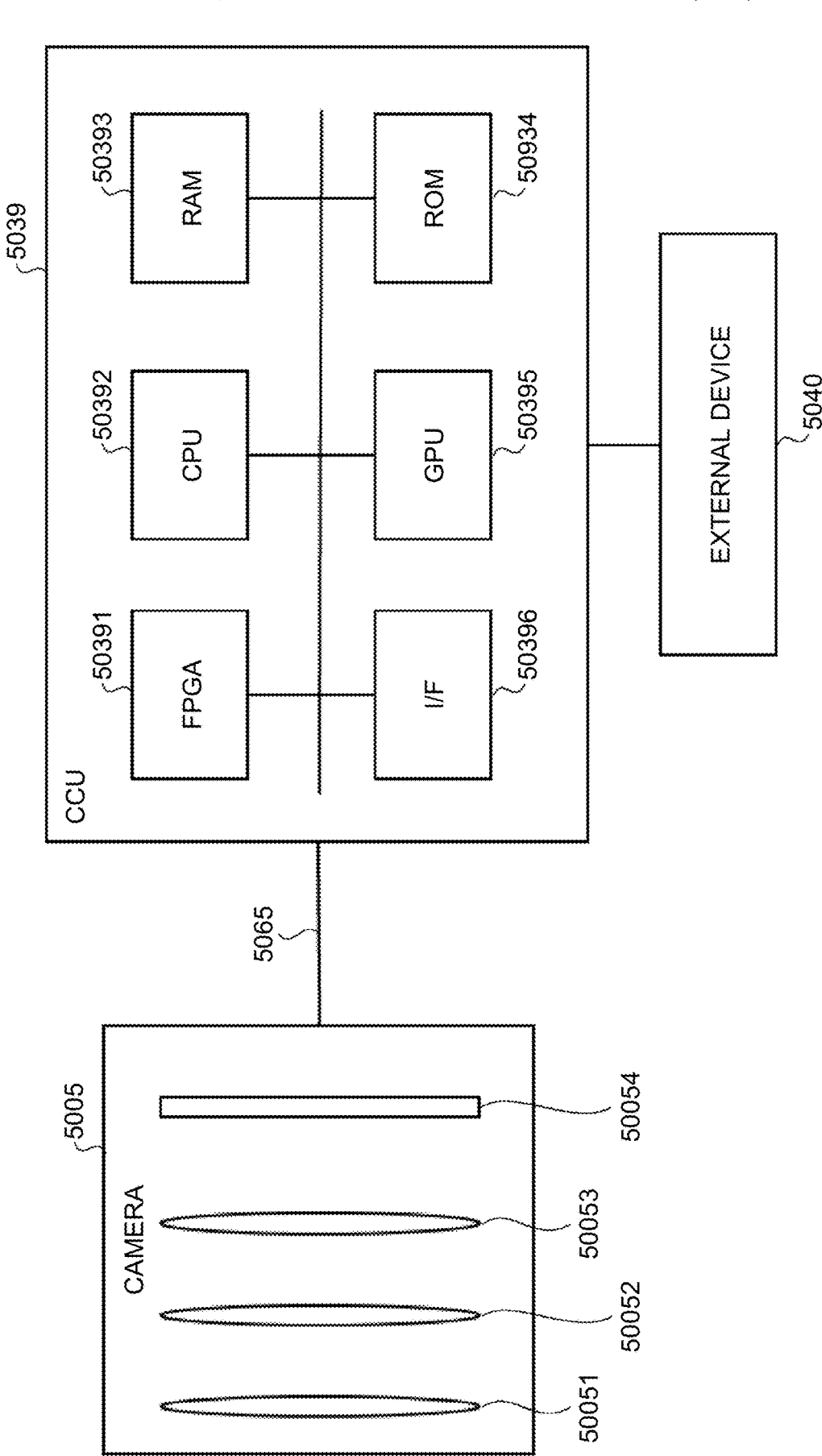
FIG. 17 is a block diagram illustrating an example of a functional configuration of a camera and a camera control unit (CCU) illustrated in FIG. 16.

An example of the endoscope system will be described using FIGS. 16 and 17. FIG. 16 is a diagram illustrating an example of a schematic configuration of an endoscope system 5000 to which the technology according to the present disclosure is applicable. FIG. 17 is a diagram illustrating an example of a configuration of an endoscope 5001 and a camera control unit (CCU) 5039. FIG. 16 illustrates a situation where an operator (for example, a doctor) 5067 who is a participant of an operation performs the operation on a patient 5071 on a patient bed 5069 using the endoscope system 5000. As illustrated in FIG. 16, the endoscope system 5000 includes the endoscope 5001 that is a medical imaging device, the CCU 5039, a light source device 5043, a recording device 5053, an output device 5055, and a support device 5027 for supporting the endoscope 5001.

In endoscopic surgery, insertion assisting tools called trocars 5025 are punctured into the patient 5071. Then, a scope 5003 connected to the endoscope 5001 and surgical tools 5021 are inserted into a body of the patient 5071 through the trocars 5025. The surgical tools 5021 include: an energy device such as an electric scalpel; and forceps, for example.

A surgical image that is a medical image in which the inside of the body of the patient 5071 is captured by the endoscope 5001 is displayed on a display device 5041. The operator 5067 performs a procedure on a surgical target using the surgical tools 5021 while viewing the surgical image displayed on the display device 5041. The medical image is not limited to the surgical image, and may be a diagnostic image captured during diagnosis.

[Endoscope]

The endoscope 5001 is an imaging section for capturing the inside of the body of the patient 5071, and is, for example, as illustrated in FIG. 17, a camera 5005 including a condensing optical system 50051 for condensing incident light, a zooming optical system 50052 capable of optical zooming by changing a focal length of the imaging section, a focusing optical system 50053 capable of focus adjustment by changing the focal length of the imaging section, and a light receiving sensor 50054. The endoscope 5001 condenses the light through the connected scope 5003 on the light receiving sensor 50054 to generate a pixel signal, and outputs the pixel signal through a transmission system to the CCU 5039. The scope 5003 is an insertion part that includes an objective lens at a distal end and guides the light from the connected light source device 5043 into the body of the patient 5071. The scope 5003 is, for example, a rigid scope for a rigid endoscope and a flexible scope for a flexible endoscope. The scope 5003 may be a direct viewing scope or an oblique viewing scope. The pixel signal only needs to be a signal based on a signal output from a pixel, and is, for example, a raw signal or an image signal. The transmission system connecting the endoscope 5001 to the CCU 5039 may include a memory, and the memory may store parameters related to the endoscope 5001 and the CCU 5039. The memory may be disposed at a connection portion of the transmission system or on a cable. For example, the memory of the transmission system may store the parameters before shipment of the endoscope 5001 or the parameters changed when current is applied, and an operation of the endoscope may be changed based on the parameters read from the memory. A set of the camera and the transmission system may be referred to as an endoscope. The light receiving sensor 50054 is a sensor for converting the received light into the pixel signal, and is, for example, a complementary metal-oxide-semiconductor (CMOS) imaging sensor. The light receiving sensor 50054 is preferably an imaging sensor having a Bayer array capable of color imaging. The light receiving sensor 50054 is also preferably an imaging sensor having a number of pixels corresponding to a resolution of, for example, 4K (3840 horizontal pixels×2160 vertical pixels), 8K (7680 horizontal pixels×4320 vertical pixels), or square 4K (3840 or more horizontal pixels×3840 or more vertical pixels). The light receiving sensor 50054 may be one sensor chip, or a plurality of sensor chips. For example, a prism may be provided to separate the incident light into predetermined wavelength bands, and the wavelength bands may be imaged by different light receiving sensors. A plurality of light receiving sensors may be provided for stereoscopic viewing. The light receiving sensor 50054 may be a sensor having a chip structure including an arithmetic processing circuit for image processing, or may be a sensor for time of flight (ToF). The transmission system is, for example, an optical fiber cable system or a wireless transmission system. The wireless transmission only needs to be capable of transmitting the pixel signal generated by the endoscope 5001, and, for example, the endoscope 5001 may be wirelessly connected to the CCU 5039, or the endoscope 5001 may be connected to the CCU 5039 via a base station in an operating room. At this time, the endoscope 5001 may transmit not only the pixel signal, but also simultaneously information (for example, a processing priority of the pixel signal and/or a synchronization signal) related to the pixel signal. In the endoscope, the scope may be integrated with the camera, and the light receiving sensor may be provided at the distal end of the scope.

[Camera Control Unit (CCU)]

The CCU 5039 is a control device for controlling the endoscope 5001 and the light source device 5043 connected to the CCU 5039 in an integrated manner, and is, for example, as illustrated in FIG. 17, an image processing device including a field-programmable gate array (FPGA) 50391, a central processing unit (CPU) 50392, a random access memory 50393, a read-only memory (ROM) 50394, a graphics processing unit (GPU) 50395, and an interface (I/F) 50396. The CCU 5039 may control the display device 5041, the recording device 5053, and the output device 5055 connected to the CCU 5039 in an integrated manner. The CCU 5039 controls, for example, irradiation timing, irradiation intensity, and a type of an irradiation light source of the light source device 5043. The CCU 5039 also performs image processing, such as development processing (for example, demosaic processing) and correction processing, on the pixel signal output from the endoscope 5001, and outputs the processed image signal (for example, an image) to an external device such as the display device 5041. The CCU 5039 also transmits a control signal to the endoscope 5001 to control driving of the endoscope 5001. The control signal is information on an imaging condition such as a magnification or the focal length of the imaging section. The CCU 5039 may have a function to down-convert the image, and may be configured to be capable of simultaneously outputting a higher-resolution (for example, 4K) image to the display device 5041 and a lower-resolution (for example, high-definition (HD)) image to the recording device 5053.

The CCU 5039 may be connected to external equipment (such as a recording device, a display device, an output device, and a support device) via an IP converter for converting the signal into a predetermined communication protocol (such as the Internet Protocol (IP)). The connection between the IP converter and the external equipment may be established using a wired network, or a part or the whole of the network may be established using a wireless network. For example, the IP converter on the CCU 5039 side may have a wireless communication function, and may transmit the received image to an IP switcher or an output side IP converter via a wireless communication network, such as the fifth-generation mobile communication system (5G) or the sixth-generation mobile communication system (6G).

[Light Source Device]

The light source device 5043 is a device capable of emitting the light having predetermined wavelength bands, and includes, for example, a plurality of light sources and a light source optical system for guiding the light of the light sources. The light sources are, for example, xenon lamps, light-emitting diode (LED) light sources, or laser diode (LD) light sources. The light source device 5043 includes, for example, the LED light sources corresponding to three respective primary colors of red (R), green (G), and blue (B), and controls output intensity and output timing of each of the light sources to emit white light. The light source device 5043 may include a light source capable of emitting special light used for special light observation, in addition to the light sources for emitting normal light for normal light observation. The special light is light having a predetermined wavelength band different from that of the normal light being light for the normal light observation, and is, for example, near-infrared light (light having a wavelength of 760 nm or longer), infrared light, blue light, or ultraviolet light. The normal light is, for example, the white light or green light. In narrow band imaging that is a kind of special light observation, blue light and green light are alternately emitted, and thus the narrow band imaging can image a predetermined tissue such as a blood vessel in a mucosal surface at high contrast using wavelength dependence of light absorption in the tissue of the body. In fluorescence observation that is a kind of special light observation, excitation light is emitted for exciting an agent injected into the tissue of the body, and fluorescence emitted by the tissue of the body or the agent as a label is received to obtain a fluorescent image, and thus the fluorescence observation can facilitate the operator to view, for example, the tissue of the body that is difficult to be viewed by the operator with the normal light. For example, in fluorescence observation using the infrared light, the infrared light having an excitation wavelength band is emitted to an agent, such as indocyanine green (ICG), injected into the tissue of the body, and the fluorescence light from the agent is received, whereby the fluorescence observation can facilitate viewing of a structure and an affected part of the tissue of the body. In the fluorescence observation, an agent (such as 5-aminolevulinic acid (5-ALA)) may be used that emits fluorescence in a red wavelength band by being excited by the special light in a blue wavelength band. The type of the irradiation light of the light source device 5043 is set by control of the CCU 5039. The CCU 5039 may have a mode of controlling the light source device 5043 and the endoscope 5001 to alternately perform the normal light observation and the special light observation. At this time, information based on a pixel signal obtained by the special light observation is preferably superimposed on a pixel signal obtained by the normal light observation. The special light observation may be an infrared light observation to observe a site inside the surface of an organ and a multi-spectrum observation utilizing hyperspectral spectroscopy. A photodynamic therapy may be incorporated.

[Recording Device]

The recording device 5053 is a device for recording the pixel signal (for example, an image) acquired from the CCU 5039, and is, for example, a recorder. The recording device 5053 records an image acquired from the CCU 5039 in a hard disk drive (HDD), a Super Density Disc (SDD), and/or an optical disc. The recording device 5053 may be connected to a network in a hospital to be accessible from equipment outside the operating room. The recording device 5053 may have a down-convert function or an up-convert function.

[Display Device]

The display device 5041 is a device capable of displaying the image, and is, for example, a display monitor. The display device 5041 displays a display image based on the pixel signal acquired from the CCU 5039. The display device 5041 may include a camera and a microphone to function as an input device that allows instruction input through gaze recognition, voice recognition, and gesture.

[Output Device]

The output device 5055 is a device for outputting the information acquired from the CCU 5039, and is, for example, a printer. The output device 5055 prints, for example, a print image based on the pixel signal acquired from the CCU 5039 on a sheet of paper.

[Support Device]

The support device 5027 is an articulated arm including a base 5029 including an arm control device 5045, an arm 5031 extending from the base 5029, and a holding part 5032 mounted at a distal end of the arm 5031. The arm control device 5045 includes a processor such as a CPU, and operates according to a predetermined computer program to control driving of the arm 5031. The support device 5027 uses the arm control device 5045 to control parameters including, for example, lengths of links 5035 constituting the arm 5031 and rotation angles and torque of joints 5033 so as to control, for example, the position and attitude of the endoscope 5001 held by the holding part 5032. This control can change the position or attitude of the endoscope 5001 to a desired position or attitude, makes it possible to insert the scope 5003 into the patient 5071, and can change the observed area in the body. The support device 5027 functions as an endoscope support arm for supporting the endoscope 5001 during the operation. Thus, the support device 5027 can play a role of a scopist who is an assistant holding the endoscope 5001. The support device 5027 may be a device for holding a microscope device 5301 to be described later, and can be called a medical support arm. The support device 5027 may be controlled using an autonomous control method by the arm control device 5045, or may be controlled using a control method in which the arm control device 5045 performs the control based on input of a user. The control method may be, for example, a master-slave method in which the support device 5027 serving as a slave device (replica device) that is a patient cart is controlled based on a movement of a master device (primary device) that is an operator console at a hand of the user. The support device 5027 may be remotely controllable from outside the operating room.

The example of the endoscope system 5000 to which the technology according to the present disclosure is applicable has been described above. For example, the technology according to the present disclosure may be applied to a microscope system.

[Microscope System]

Figure 18:
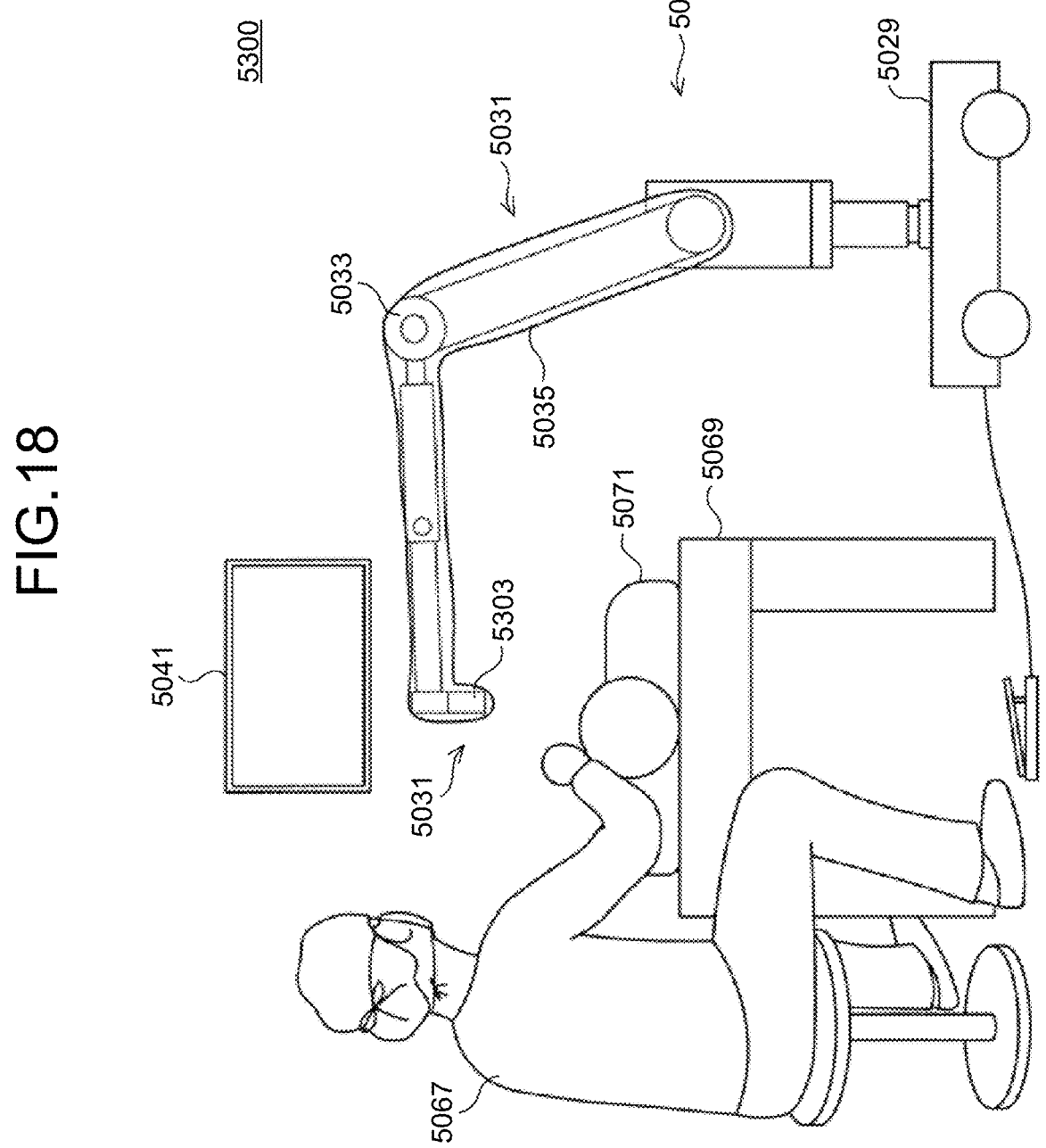
FIG. 18 is a diagram illustrating an example of a schematic configuration of a microscopic surgery system.

FIG. 18 is a diagram illustrating an example of a schematic configuration of a microscopic surgery system 5300 to which the technology according to the present disclosure is applicable. In the following description, the same components as those of the endoscope system 5000 will be denoted by the same reference numerals, and the description thereof will not be repeated.

FIG. 18 schematically illustrates a situation where the operator 5067 performs an operation on the patient 5071 on the patient bed 5069 using a microscopic surgery system 5300. For the sake of simplicity, FIG. 18 does not illustrate a cart 5037 among the components of the microscopic surgery system 5300, and illustrates the microscope device 5301 instead of the endoscope 5001 in a simplified manner. The microscope device 5301 may refer to a microscope 5303 provided at the distal end of the links 5035, or may refer to the overall configuration including the microscope 5303 and the support device 5027.

As illustrated in FIG. 18, during the operation, the microscopic surgery system 5300 is used to display an image of a surgical site captured by the microscope device 5301 in a magnified manner on the display device 5041 installed in the operating room. The display device 5041 is installed in a position facing the operator 5067, and the operator 5067 performs various procedures, such as excision of an affected part, on the surgical site while observing the state of the surgical site using the image displayed on the display device 5041. The microscopic surgery system 5300 is used in, for example, ophthalmic operation and neurosurgical operation.

The respective examples of the endoscope system 5000 and the microscopic surgery system 5300 to which the technology according to the present disclosure is applicable have been described above. Systems to which the technology according to the present disclosure is applicable are not limited to such examples. For example, the support device 5027 can support, at the distal end thereof, another observation device or another surgical tool instead of the endoscope 5001 or the microscope 5303. Examples of the other applicable observation device include forceps, tweezers, a pneumoperitoneum tube for pneumoperitoneum, and an energy treatment tool for incising a tissue or sealing a blood vessel by cauterization. By using the support device to support the observation device or the surgical tool described above, the position thereof can be more stably fixed and the load of the medical staff can be lower than in a case where the medical staff manually supports the observation device or the surgical tool. The technology according to the present disclosure may be applied to a support device for supporting such a component other than the microscope.

The technology according to the present disclosure can be suitably applied to medical observation systems such as the endoscope system 5000 and the microscopic surgery system 5300. By applying the technology according to the present disclosure to the medical observation system, it is possible to appropriately estimate external force without using a torque sensor or a force sensor. Here, for example, the endoscope 5001 corresponds to the endoscope 200 according to the one embodiment. The support device 5027 corresponds to the robot 11 according to the one embodiment. The actuator 50 according to the one embodiment is applied to the holding part 5032, the joint 5033, and the like of the support device 5027. The arm control device 5045 corresponds to the control device 20 according to the one embodiment.

4. Configuration Example of Hardware

Figure 19:
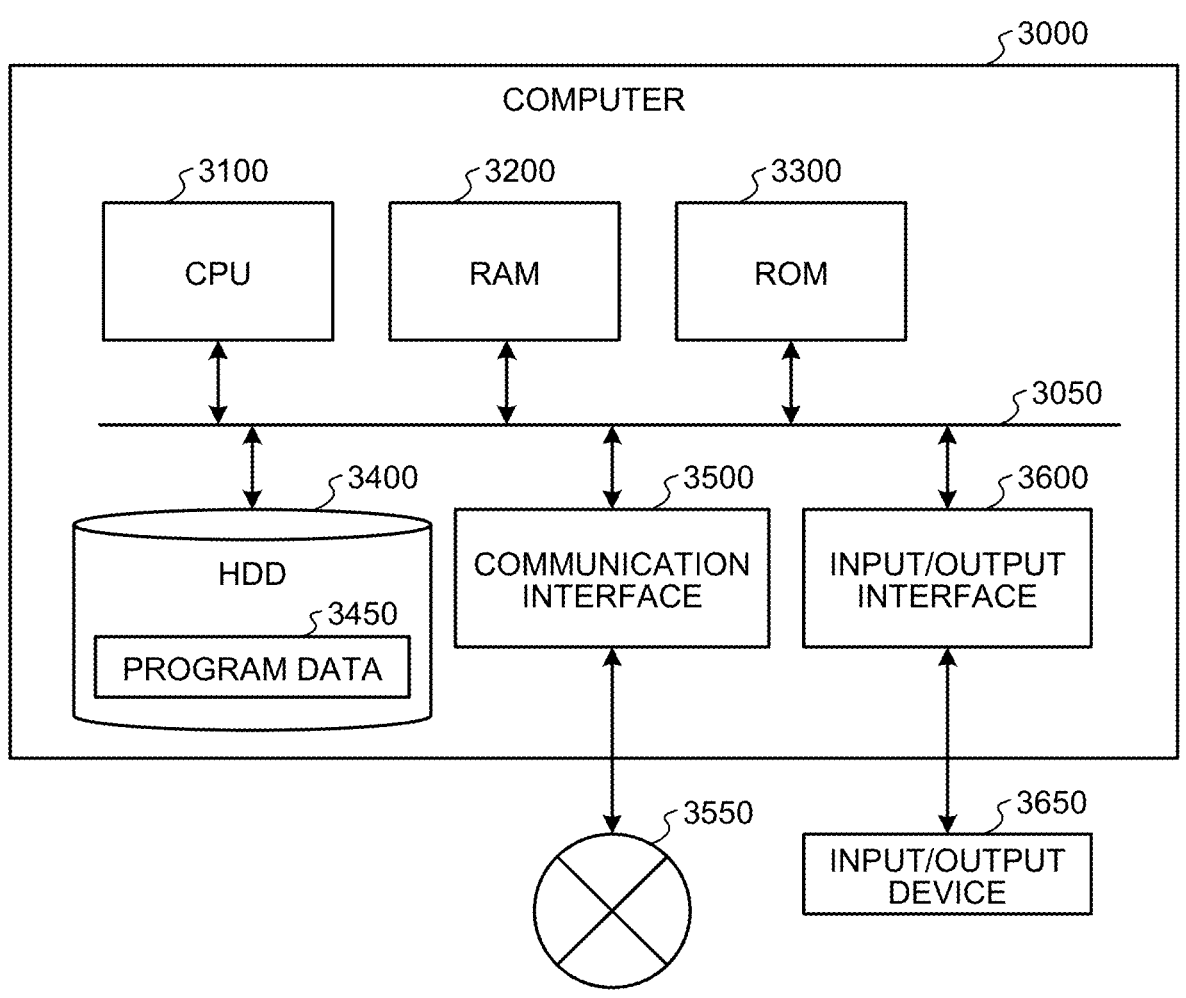
FIG. 19 is a diagram illustrating an example of a schematic configuration of hardware.

The information processing device such as the CCU 1039 described above is realized by, for example, a computer 3000 having a configuration in a manner illustrated in FIG. 19. FIG. 19 is a diagram illustrating a schematic configuration of hardware of the computer 3000.

As illustrated in FIG. 19, the computer 3000 includes a CPU 3100, a RAM 3200, a read only memory (ROM) 3300, a hard disk drive (HDD) 3400, a communication interface 3500, and an input/output interface 3600. Each section of the computer 3000 is connected by a bus 3050.

The CPU 3100 operates on the basis of programs stored in the ROM 3300 or the HDD 3400, and controls each section. For example, the CPU 3100 expands the programs, which are stored in the ROM 3300 or the HDD 3400, in the RAM 3200 and executes processing corresponding to the various programs.

The ROM 3300 stores a boot program such as a basic input output system (BIOS) executed by the CPU 3100 during activation of the computer 3000, a program that depends on hardware of the computer 3000, and the like.

The HDD 3400 is a recording medium that can be read by the computer 3000 and that non-temporarily records the programs executed by the CPU 3100, data used by the programs, and the like. Specifically, the HDD 3400 is a recording medium that records an information processing program according to the present disclosure which program is an example of program data 3450.

The communication interface 3500 is an interface for the computer 3000 to connect to an external network 3550 (such as the Internet). For example, via the communication interface 3500, the CPU 3100 receives data from another equipment or transmits data generated by the CPU 3100 to another equipment.

The input/output interface 3600 is an interface to connect an input/output device 3650 and the computer 3000. For example, the CPU 3100 receives data from an input device such as a keyboard or mouse via the input/output interface 3600. Furthermore, the CPU 3100 transmits data to an output device such as a display, a speaker, or a printer via the input/output interface 3600. Furthermore, the input/output interface 3600 may function as a medium interface that reads a program or the like recorded on a predetermined recording medium (medium). The medium is, for example, an optical recording medium such as a digital versatile disc (DVD) or phase change rewritable disk (PD), a magneto-optical recording medium such as a magneto-optical disk (MO), a tape medium, a magnetic recording medium, a semiconductor memory, or the like.

For example, in a case where the computer 3000 functions as the CCU 1039, the CPU 3100 of the computer 3000 realizes the functions of each section of the CCU 1039 by executing an information processing program loaded on the RAM 3200. In addition, the HDD 3400 stores the information processing program and various kinds of data. Note that the CPU 3100 reads the program data 3450 from the HDD 3400 and performs execution thereof. However, these programs may be acquired from another device via the external network 3550 in another example.

Although the embodiments, modification examples, and application examples of the present disclosure have been described in detail with reference to the accompanying drawings, the technical scope of the present disclosure is not limited to such examples. It is obvious that a person with an ordinary skill in a technological field of the present disclosure can conceive of various modification examples or correction examples within the scope of technical ideas described in claims, and it should be understood that these also naturally belong to the technical scope of the present disclosure.

5. Appendix

Note that the present technology can also have the following configurations.

(1)

A control system comprising:

a robot having an actuator; and an estimation section that estimates external force received by the robot on a basis of state information of the robot, wherein the actuator includes an encoder on an output shaft side, a speed reducer coupled to the encoder on the output shaft side and having backdrivability, a motor coupled to the speed reducer, and an encoder on an input shaft side which encoder is coupled to the motor.

(2)

The control system according to (1), wherein the estimation section estimates the external force received by the robot by subtracting a disturbance estimation value of when it is assumed that the robot is in an unloaded state from a disturbance estimation value of when the robot is in a loaded state.

(3)

The control system according to (2), wherein the disturbance estimation value of when the robot is in the loaded state is a disturbance estimation value of a disturbance observer.

(4)

The control system according to (2) or (3), wherein the estimation section uses a learned model and acquires the disturbance estimation value of when it is assumed that the robot is in the unloaded state, and the learned model outputs, when state information of the robot is input, the disturbance estimation value of when it is assumed that the robot is in the unloaded state.

(5)

The control system according to (4), wherein the learned model includes a long short-term memory (LSTM) block, and the state information of the robot is time-series information.

(6)

The control system according to (4), wherein the learned model is a model acquired by an input of time-series information of an acceleration reference value of an input shaft and an angle and an angular velocity of an input/output shaft to a neural network.

(7)

The control system according to any one of (1) to (6), wherein the estimation section estimates external force received by a joint section or a distal end of the robot.

(8)

The control system according to any one of (1) to (6), wherein the robot includes a joint section having the actuator, the state information of the robot includes a torque reference value, an angle, and an angular velocity of the joint section, and the estimation section estimates external force received by the joint section.

(9)

The control system according to any one of (1) to (6), wherein the robot includes a distal end having the actuator, the state information of the robot includes an acceleration reference value, a position, and a speed of the distal end, and the estimation section estimates external force received by the distal end.

(10)

The control system according to any one of (7) to (9), wherein the robot includes an arm.

(11)

The control system according to any one of (1) to (10), wherein the speed reducer is a speed reducer having forward driving efficiency of 60% or more.

(12)

The control system according to any one of (1) to (11), wherein the speed reducer is a speed reducer having a backlash lower than a predetermined value.

(13)

The control system according to any one of (1) to (11), wherein the speed reducer is a speed reducer having no backlash.

(14)

The control system according to any one of (1) to (13), wherein the speed reducer includes a plurality of gears, and the plurality of gears has coating layers that reduce friction on outer peripheral sections that mesh with each other.

(15)

The control system according to any one of (1) to (14), wherein the motor is a motor in which cogging torque is 50% or less of motor rated torque.

(16)

The control system according to any one of (1) to (15), wherein the motor is a motor in which a winding wire is configured by a flexible substrate.

(17)

The control system according to any one of (1) to (16), wherein the robot is a robot that holds an endoscope.

(18)

The control system according to any one of (1) to (17), wherein the robot is a master robot or a slave robot.

(19)

A control device comprising:

an estimation section that estimates, on a basis of state information of a robot having an actuator, external force received by the robot, wherein the actuator includes an encoder on an output shaft side, a speed reducer coupled to the encoder on the output shaft side and having backdrivability, a motor coupled to the speed reducer, and an encoder on an input shaft side which encoder is coupled to the motor.

(20)

An actuator comprising:

an encoder on an output shaft side;

a speed reducer coupled to the encoder on the output shaft side and having backdrivability;

a motor coupled to the speed reducer; and an encoder on an input shaft side which encoder is coupled to the motor.

(21)

A control device including a component related to the control system according to any one of (1) to (18).

(22)

An actuator including a component related to the control system according to any one of (1) to (18).

REFERENCE SIGNS LIST

1 CONTROL SYSTEM
10 ROBOT DEVICE
11 ROBOT
11A ARM STRUCTURE
12 DETECTION SECTION
20 CONTROL DEVICE
21 DOB
22 ESTIMATION SECTION
23 CONTROL SECTION
23a POSITION CONTROLLER
23b FORCE CONTROLLER
24 STORAGE SECTION
24a LEARNED MODEL
50 ACTUATOR
51 ENCODER
52 LOAD ELEMENT
53 MOTOR
53a FLEXIBLE SUBSTRATE
54 ENCODER
60 HIGH-EFFICIENCY PLANETARY SPEED REDUCER
61 PLANETARY GEAR MECHANISM
61a SUN GEAR
61b PLANETARY GEAR
61c INTERNAL GEAR
70 ACTUATOR
71 COUPLING MECHANISM
81 ANGLE CONTROLLER
82 TORQUE CONTROLLER
83 FORCE CONTROLLER
100 BASE
101 FIRST LINK
102 SECOND LINK
103 THIRD LINK
104 FOURTH LINK
111 FIRST JOINT SECTION
112 SECOND JOINT SECTION
113 THIRD JOINT SECTION
114 VERTICAL ROTATION SHAFT SECTION
115 RIGHT-LEFT ROTATION SHAFT SECTION
116 OPTICAL-AXIS ROTATION SHAFT SECTION
200 ENDOSCOPE
201 LENS BARREL
202 CAMERA HEAD
N1 NEURAL NETWORK

The invention claimed is:

1. A control system comprising:
a robot having an actuator; and
processing circuitry configured to
estimate external force received by the robot by subtracting a disturbance estimation value of when it is assumed that the robot is in an unloaded state from a disturbance estimation value of when the robot is in a loaded state,
acquire the disturbance estimation value of when it is assumed that the robot is in the unloaded state, output, by a learned model, when state information of the robot is input, the disturbance estimation value of when it is assumed that the robot is in the unloaded state,
wherein the learned model is a model acquired by an input of time-series information of an acceleration reference value of an input shaft and an angle and an angular velocity of the input shaft and an output shaft to a neural network,
wherein the actuator includes,
an encoder on an output shaft side,
a speed reducer coupled to the encoder on the output shaft side and having backdrivability,
a motor coupled to the speed reducer, and
an encoder on an input shaft side which encoder is coupled to the motor.

2. The control system according to claim 1, wherein the disturbance estimation value of when the robot is in the loaded state is a disturbance estimation value of a disturbance observer.

3. The control system according to claim 1, wherein the learned model includes a long short-term memory (LSTM) block, and
the state information of the robot is time-series information.

4. The control system according to claim 1, wherein the processing circuitry is further configured to
estimate external force received by a joint section or a distal end of the robot.

5. The control system according to claim 4, wherein the robot includes an arm.

6. The control system according to claim 1, wherein the robot includes a joint section having the actuator,
the state information of the robot includes a torque reference value, an angle, and an angular velocity of the joint section, and
the processing circuitry is further configured to estimate external force received by the joint section.

7. The control system according to claim 1, wherein the robot includes a distal end having the actuator,
the state information of the robot includes an acceleration reference value, a position, and a speed of the distal end, and
the processing circuitry is further configured to estimate external force received by the distal end.

8. The control system according to claim 1, wherein the speed reducer is a speed reducer having forward driving efficiency of 60% or more.

9. The control system according to claim 1, wherein the speed reducer is a speed reducer having a backlash lower than a predetermined value.

10. The control system according to claim 1, wherein the speed reducer is a speed reducer having no backlash.

11. The control system according to claim 1, wherein the speed reducer includes a plurality of gears, and
the plurality of gears has coating layers that reduce friction on outer peripheral sections that mesh with each other.

12. The control system according to claim 1, wherein the motor is a motor in which cogging torque is 50% or less of motor rated torque.

13. The control system according to claim 1, wherein the motor is a motor in which a winding wire is configured by a flexible substrate.

14. The control system according to claim 1, wherein the robot is a robot that holds an endoscope.

15. The control system according to claim 1, wherein the robot is a master robot or a slave robot.

16. A control device comprising:

processing circuitry configured to estimate external force received by a robot by subtracting a disturbance estimation value of when it is assumed that the robot is in an unloaded state from a disturbance estimation value of when the robot is in a loaded state, acquire the disturbance estimation value of when it is assumed that the robot is in the unloaded state, output, by a learned model, when state information of the robot is input, the disturbance estimation value of when it is assumed that the robot is in the unloaded state, wherein the learned model is a model acquired by an input of time-series information of an acceleration reference value of an input shaft and an angle and an angular velocity of the input shaft and an output shaft to a neural network, wherein an actuator includes an encoder on an output shaft side, a speed reducer coupled to the encoder on the output shaft side and having backdrivability, a motor coupled to the speed reducer, and an encoder on an input shaft side which encoder is coupled to the motor.

* * * * *